(12) United States Patent
Tunius

(10) Patent No.: US 11,414,576 B2
(45) Date of Patent: Aug. 16, 2022

(54) POLYURETHANE BASED SWITCHABLE ADHESIVES

(71) Applicant: Lumina Adhesives AB, Gothenburg (SE)

(72) Inventor: Mats Tunius, Gothenburg (SE)

(73) Assignee: Lumina Adhesives AB, Gothenburg (SE)

( * ) Notice: Subject to any disclaimer, the term of this patent is extended or adjusted under 35 U.S.C. 154(b) by 794 days.

(21) Appl. No.: 15/549,158

(22) PCT Filed: Feb. 5, 2016

(86) PCT No.: PCT/EP2016/025006
§ 371 (c)(1),
(2) Date: Aug. 5, 2017

(87) PCT Pub. No.: WO2016/124339
PCT Pub. Date: Aug. 11, 2016

(65) Prior Publication Data
US 2018/0030321 A1    Feb. 1, 2018

(30) Foreign Application Priority Data
Feb. 5, 2015  (GB) ..................................... 1501965

(51) Int. Cl.
| | | |
|---|---|---|
| *C09J 175/08* | (2006.01) | |
| *C08G 18/48* | (2006.01) | |
| *C08F 290/06* | (2006.01) | |
| *A61B 46/20* | (2016.01) | |
| *A61F 13/02* | (2006.01) | |
| *C08G 18/62* | (2006.01) | |
| *C08G 18/79* | (2006.01) | |
| *C09J 175/04* | (2006.01) | |
| *C08G 18/10* | (2006.01) | |
| *C08G 18/81* | (2006.01) | |
| *C08G 18/24* | (2006.01) | |
| *C08G 18/73* | (2006.01) | |

(52) U.S. Cl.
CPC ............ *C09J 175/08* (2013.01); *A61B 46/20* (2016.02); *A61F 13/0206* (2013.01); *A61F 13/0253* (2013.01); *C08F 290/067* (2013.01); *C08G 18/10* (2013.01); *C08G 18/244* (2013.01); *C08G 18/4829* (2013.01); *C08G 18/6229* (2013.01); *C08G 18/73* (2013.01); *C08G 18/792* (2013.01); *C08G 18/8116* (2013.01); *C09J 175/04* (2013.01); *A61B 2046/205* (2016.02)

(58) Field of Classification Search
CPC .. C09J 175/08; C08F 290/067; C08G 18/792; C08G 18/10; C08G 18/8116; C08G 18/244; C08G 18/73; C08G 18/4829; C08G 18/6229; A61B 46/20; A61B 2046/205; A61F 13/0253
See application file for complete search history.

(56) References Cited

U.S. PATENT DOCUMENTS

| | | |
|---|---|---|
| 6,610,762 B1 | 8/2003 | Webster |
| 2012/0059124 A1 | 3/2012 | Shimazaki et al. |
| 2012/0100326 A1* | 4/2012 | Sherman ................ C09J 151/08 428/41.8 |
| 2014/0087180 A1 | 3/2014 | Maruyama et al. |
| 2015/0340848 A1* | 11/2015 | Nakashima .......... H02G 15/003 174/72 A |

FOREIGN PATENT DOCUMENTS

| | | |
|---|---|---|
| CN | 103249795 | 8/2013 |
| EP | 2371920 | 10/2011 |
| EP | 2371920 A1 | 10/2011 |
| JP | 2009221249 | 10/2009 |
| WO | 9706836 A2 | 2/1997 |

OTHER PUBLICATIONS

PCT, International Search Report and Written Opinion for International Application No. PCT/EP2016/025006, dated May 13, 2016, 9 pages.

* cited by examiner

*Primary Examiner* — Jessica M Roswell
(74) *Attorney, Agent, or Firm* — Lowenstein Sandler LLP

(57) ABSTRACT

Switchable adhesive compositions are disclosed comprising an adhesive component, which is formed from a material or materials capable of undergoing cross-linking with isocyanale other than by free radical polymerisation and at least one isocyanate having an average of more than one isocyanate functions, unsaturated curable molecules mixed in or partially bound in with the adhesive component, or unsaturated curable moieties fully bound in to the material or materials capable of undergoing cross-linking with isocyanate, and a photoinitiator. The adhesive composition forms a tacky gel-like pressure sensitive adhesive that is capable of moulding to a substrate, and upon activation of the photoinitiator the curable molecules or moieties cross-link to form a dense 3-dimensional network through the adhesive component which causes the composition to become less tacky and to form an elastic film with reduced peel strength.

46 Claims, 11 Drawing Sheets

POLYURETHANE BASED SWITCHABLE ADHESIVES

CROSS-REFERENCE TO RELATED APPLICATIONS

This application is a national stage entry under 35 U.S.C. § 371 of International Application No. PCT/GB2016/025006, filed Feb. 5, 2016, which claims the benefit of priority of GB Application No. 1501965.6, filed Feb. 5, 2015, the disclosures of which are hereby incorporated by reference herein in their entirety.

FIELD OF THE INVENTION

The present invention relates to adhesive compositions, more particularly to polyurethane based pressure sensitive adhesive compositions which are "switchable" from a tacky state to a non-tacky or low-tack state such that the switched adhesive has a reduced peel strength. The present invention also relates to methods for producing such switchable adhesive compositions and to articles comprising such switchable adhesive compositions. The invention also relates to methods of treatment using adhesive medical products on patients with an injury or a long-term medical condition requiring repeated application of dressings and to methods of treatment for patients undergoing surgery, or for patients after surgery and/or injury requiring a skin covering, as well as for skin closure applications.

For convenience, the term "switchable" will be used to refer to adhesive compositions which can be changed from a tacky to a non-tacky state or, more accurately, to a low-tack state. Recognizing that the expression "low-tack" is a relative term, it will be defined here as meaning the condition of minimum tackiness which the adhesive composition reaches after switching from its tacky state. The reduction in peel force may be as great as 99% or as little as 30%. Typically, the reduction in peel force is around 99% on HDPE and around 90% on skin.

The present invention provides benefits in situations where strong adhesion to fragile surfaces is required. Should it become necessary to release the fragile surface, the adhesive composition can be switched from its tacky state to its low-tack state and removed from the fragile surface completely without harming it.

BACKGROUND OF THE INVENTION

Certain adhesive medical products, such as adhesive surgical or medical dressings and bandages normally comprise a layer of a pressure sensitive adhesive. However, when a conventional adhesive dressing and/or bandage is removed from the patient's skin, it can often cause localised trauma and/or pain to the patient. This is particularly true for patients with a long term condition that requires an adhesive dressing to be applied to the same part of the body repeatedly over a prolonged period, such as stoma patients. It is also true for patients with fragile skin, especially the elderly and children.

Therefore, a need has been identified to provide adhesive medical products, such as dressings, which are able to undergo a reduction in peel strength of the adhesive and which therefore cause less localised trauma to the patient's skin upon removal, compared to an adhesive medical product that uses a conventional adhesive. Further, a need has been identified to provide such adhesive medical products where the reduction in peel strength can be achieved in a controlled manner in a relatively short time, say from a number of seconds to a few minutes.

The present invention is also applicable to other types of adhesive medical products, such as surgical incision drapes, bacterial barriers for covering wounds and skin closure devices. In these types of applications, the adhesive medical product is left on the skin after switching and is not removed with the backing layer. Rather, the backing layer is a release liner which is specially treated to be more slippery than skin so that the switched adhesive layer remains preferentially on the skin surface.

Examples of known switchable adhesives are disclosed in U.S. Pat. Nos. 5,032,637, 5,352,516, 4,331,576 and 5,182,323 which describe adhesives that become less tacky, i.e., are switchable, upon contact with water. However, such adhesives are unsuitable if used on a wound dressing and the patient's wound needs to be kept dry.

United States Patent Application No. US 2013/0123678 A1 and related International Patent Applications Nos. WO 2010/129299 A2 and WO 2013/066401 A1 disclose multi-layer laminates that are selectively releasable from a substrate upon application of an agent to an outer face or perimeter of the laminate and appropriate contacting between the agent and the adhesive. The laminate comprises an interior layer defining a plurality of fluid passageway conduits or apertures extending through the interior layer, the interior layer defining a bottom surface and an oppositely directed top surface, an adhesive layer disposed along the bottom surface of the interior layer and a carrier layer disposed on the top surface of the interior layer. Upon contacting the adhesive layer to the substrate, the laminate is adhesively adhered thereto. Upon removal of the cover layer from the laminate, the interior layer and plurality of fluid passageway conduits are exposed, and upon application of an effective amount of the agent to the top surface of the interior layer, transport of the agents to the adhesive and passage of sufficient contact time between the agent and the adhesive, the adhesively adhered laminate can be easily removed from the substrate. The agent may be an adhesive deactivating agent selected from silicones, perfluoroalkyl derivatives, low molecular weight oils, aqueous compositions, alkyl esters, limonene derivatives, paraffin solvents, hydrocarbon solvents, alkyl ethers, aromatic esters, surfactants and combinations thereof.

European Patent No. EP 0863775 and U.S. Pat. Nos. 6,184,264 and 6,610,762 disclose adhesives which are switchable when exposed to, inter alia, visible light, i.e., are visible light switchable or are switchable upon exposure to low dosages of UV light. The visible light switchable or low dosage UV light switchable adhesives described in these documents generally comprise an acrylic adhesive based on copolymers of alkyl acrylates, acrylic acid and/or a free radical polymerisable vinyl moiety "modified" or functionalised by a curable moiety bound thereto. Typical of the bound-in curable moieties are those derived from anthracenes, cinnamates, maleimides, coumarins, acrylates and/or methacrylates.

U.S. Pat. No. 4,999,242 discloses an adhesive tape having an adhesive curable by irradiation, for example by ultra violet rays or ionising radiation such as an electron beam, comprising a radiation-curable adhesive layer which is formed on a radiation transmitting-substrate. The radiation-curable adhesive layer is composed of an acrylic adhesive, a compound having carbon-carbon double bonds and a silicone acrylate compound. The radiation-curable tape can be used in processing steps for the production of semiconductor wafers, ceramics and glass employing a direct picking-up system.

U.S. Pat. No. 5,955,512 discloses a pressure sensitive adhesive composition comprising an acrylic copolymer (A), an energy beam polymerizable urethane acrylate oligomer (B) and an energy beam polymerizable compound having one acryloyl group or methacryloyl group in each molecule thereof (C). The composition preferably also contains a plasticizer (D), a crosslinking agent (E) and/or a photo-polymerization initiator (F) according to necessity. The pressure sensitive adhesive composition has satisfactory pressure sensitive adherence and initial adhesion before irradiation with an energy beam and the adhesive strength thereof is sharply reduced whilst maintaining its elasticity after irradiation. The pressure sensitive adhesive composition is said to ensure excellent chip alignability in the expanding step subsequent to dicing.

One problem associated with known switchable adhesives is that, in their tacky state, they are not repositionable. Once applied to a substrate (e.g. skin), the adhesive remains firmly stuck to the substrate until switched. This can be inconvenient and/or wasteful because, if an adhesive medical product is applied in an incorrect position, it can only be removed after switching of the adhesive to its non-tacky or low-tack state. If it is removed without switching of the adhesive, it is painful for the patient and, in any case, the adhesive medical product cannot be re-used because the adhesive layer will be contaminated with the patient's skin cells and/or hair and will also be insufficiently tacky for re-use as a result.

SUMMARY OF THE INVENTION

The present invention has been made in view of the above disadvantages of known switchable pressure sensitive adhesive systems and provides the following advantages:
- A gel like behavior similar to silicon adhesives but with a higher peel adhesion.
- A switched value on skin of 0.1-0.2 N/20 mm, which is about 5 times lower than for polyacrylate-based switchable adhesives.
- Repositionable before switch. The switchable adhesive composition in its unswitched form is removable from a destination surface to which it has been attached for repositioning. The gel-like consistency of the unswitched adhesive composition means that it can be peeled away from the destination surface on a backing layer to which the adhesive adheres preferentially. The adhesive composition becomes extruded and forms "strings" which detach from the surface cleanly without any appreciable loss of tackiness.
- No appreciable pain, both before and after switch, when peeled from hairy surfaces.
- Low cold flow due to the gel like behavior (arising from the loosely formed three-dimensional network) compared to polyacrylate-based switchable adhesives.
- Can be manufactured without the use of solvents,
- A switch time of about 1 or 1.5-2 seconds which is around twice as fast as comparable polyacrylate-based switchable adhesives.

An embodiment of the present invention provides an improved switchable adhesive system which undergoes transformation from a tacky state to a non-tacky state in a relatively short period of time compared to known switchable adhesive systems. An embodiment of the present invention provides an improved switchable adhesive system which is repositionable. An embodiment of the present invention provides an improved switchable adhesive system which cause little or no pain when peeled from a hairy skin surface.

In a first aspect, the present invention provides a switchable adhesive composition comprising, in proportions by weight, about 5% up to about 80% of at least one curable molecule that is curable by free radical polymerisation and 0.05% to 10% of photoinitiator, the balance being an adhesive component and incidental constituents, wherein the adhesive component is composed of:
  (i) a material or materials capable of undergoing cross-linking with isocyanate other than by free radical polymerisation, said material or materials having an average of more than one functional group containing an active hydrogen atom and having a weight average molecular weight in the range 100 to 1,000,000 dalton, and
  (ii) at least one isocyanate having an average of more than one isocyanate functions to cross-link said material or materials and having a weight average molecular weight in the range 100 to 1,000,000 dalton.

Suitably, said curable molecules may comprise unsaturated compounds and, defined in an alternative way, the switchable adhesive composition of the first aspect of the present invention should comprise sufficient curable molecules to afford at least about 0.05 equivalent of double bonds per kilogram (mol/kg) based on the total weight of the adhesive composition.

In a second aspect of the invention there is provided a switchable adhesive composition comprising, in proportions by weight, 0.05% to 10% of photoinitiator, the balance being an adhesive component and incidental constituents, wherein the adhesive component is comprised of:
  (i) a material or materials capable of undergoing cross-linking with isocyanate other than by free radical polymerisation, said material or materials having an average of more than one functional group containing an active hydrogen atom, a proportion of the functional groups containing an active hydrogen atom being reacted with and bonded to a curable moiety that is curable by free radical polymerisation, such that the adhesive composition comprises up to 98% by weight of such curable moieties, and having a weight average molecular weight in the range 100 to 1,000,000 dalton, and
  (ii) at least one isocyanate having an average of more than one isocyanate functions to cross-link said material or materials and having a weight average molecular weight in the range 100 to 1,000,000 dalton.

In some embodiments, the adhesive composition may comprise up to 80% by weight of such curable moieties. Suitably, said curable moieties may comprise unsaturated groups and, when defined in an alternative way, the switchable adhesive composition of the second aspect of the present invention should comprise sufficient curable moieties to afford at least about 0.01 equivalent of double bonds per kilogram (mol/kg) based on the total weight of the adhesive composition.

By active hydrogen is meant hydrogen attached to an electronegative element in a compound, for example —OH, —NH, —SH, etc. While the material or materials capable of undergoing cross-linking with isocyanates other than by free radical polymerisation are defined herein as comprising an average of more than one functional group containing active hydrogen atom, it will be understood by those skilled in the art that in some contexts, particularly in relation to the cross-linking adhesive component that is included in the adhesive compositions of the invention, some or all of those functional groups are bonded to other moieties with removal of the active hydrogen atoms, particularly the isocyanate for cross-linking the adhesive component and, when used, the curable moieties that are susceptible to curing by free radical polymerisation. Suitably the material or materials capable of undergoing cross-linking with isocyanates other than by free radical polymerisation in either the first or second aspects of the invention may have at least two functional groups containing an active hydrogen atom.

The material or materials capable of undergoing cross-linking with isocyanate other than by free radical polymerisation may have a weight average molecular weight in the range 100 to 100,000 dalton.

Preferably, the material or materials capable of undergoing cross-linking with isocyanates is a polyol or a hydroxyl terminated compound having at least two hydroxyl functions, or a mixture of such polyols or hydroxyl terminated compounds, or is an amine terminated compound having at least two primary or secondary amine functions or a mixture of such amine terminated compounds.

Most preferably, the material capable of undergoing cross-linking with isocyanates is a polyol.

Suitably the adhesive component consists of a polyurethane adhesive. The adhesive component is suitably a pressure-sensitive adhesive.

DETAILED DESCRIPTION OF THE INVENTION

Polyol Specifications

Preferably the polyol is a polyether or a polyester polyol.

Preferably, the weight average molecular weight of the polyol is in the range 2000 to 20,000 dalton.

Preferably, the polyol has three or more hydroxyl functions. Most preferably, the polyol has an average of more than three and fewer than six hydroxyl functions. Examples of these are ethoxylated or propoxylated (optionally randomly polymerized from a mixture of ethylene oxide and propylene oxide or polymerized separately during the reaction in succession) species of ethylene glycol, propylene glycol, butyldiol, glycerol, trimethylolpropane pentaerythritol, dextrose or sorbitol, as well as di- and tri-ethers of the aforementioned species.

For medical applications, i.e. for adhesive medical products that are used in contact with skin, a polyol is selected that gives the desired rheological, moisture vapour transmission rate (MVTR), adhesion and biocompatibility properties in the final switchable adhesive composition.

Isocyanate Specifications

In some embodiments, the isocyanate may have an average of fewer than four isocyanate functions to cross-link said material.

Preferably, the weight average molecular weight of the isocyanate is in the range 100 to 2000 dalton.

Example isocyanates include hexamethylene diisocyanate, isophorone diisocyanate, toluene 2,4-diisocyanate, 4,4'-methylenebis(phenyl isocyanate), 4,4'-methylenebis(cyclohexyl isocyanate) as well as their homopolymers or diisocyanate terminated reaction products with diols e.g. mono- or polyethylene glycol, mono- or polypropylene glycol, hydroxyl terminated polyesters, etc.

A sufficient proportion of the isocyanate molecules needs to have two or more isocyanate functions in order to cross link the polyol, which is why the isocyanate is specified as having an average of more than one isocyanate functions.

In the adhesive composition of the present invention, the material or materials capable of undergoing cross-linking with isocyanate other than by free radical polymerisation is cross-linked with one or more isocyanates to give the adhesive composition a non-liquid, flowable gel-like consistency that is capable of moulding to the shape and configuration of a surface on which it is placed. The adhesive component is capable of forming polar bonds and Van de Waals bonds with the surface, which gives the adhesive component its tackiness. When the photoinitiator is activated, for example, by exposure to long wavelength UV or visible light, the curable molecules or moieties form chemical bonds with other curable molecules or moieties and create dense cross-linking. One effect of such cross-linking is to build a three-dimensional polymeric network entangling or, in the case of fully bound-in moieties, drastically increasing the crosslinking density of the adhesive's loosely formed three dimensional network, thereby reducing the polymer segments mobility and free volume. This means that upon selectively curing the curable molecules or curable moieties, the composition loses its flowability, essentially becoming an elastic film with no or little tackiness. When a conventional pressure sensitive adhesive is peeled from a surface to which it is adhered, the required energy may be about $10^2$ to $10^4$ times larger than that which would be needed from a thermodynamic perspective, as a result of internal energy losses in the PSA bulk material and because at least a component of the peeling force acts in the direction that is normal to the surface. In the switchable adhesive composition of the present invention, the dense polymeric network that is formed by the curable molecules or moieties upon activation of the photoinitiator reduces the free volume within the composition and the plasticising effect of the pre-polymer disappears, leading to a substantial decrease in the tackiness of the composition. The large reduction in the viscous component of the adhesive composition during switching causes the required peel force to be reduced that is closer to that which is implied by thermodynamic considerations alone.

Curable Molecules and Curable Moieties

The switchable adhesive composition of the present invention comprises an amount of at least one curable molecule or curable moiety. The curable molecule may be included in the adhesive composition of the invention as a mixture ("mixed-in") or may be partially bound in to the adhesive component ("partially bound-in"), by which is meant that a proportion (but not all) of the curable molecule is bound to the adhesive component, particularly to the isocyanate. In some embodiments, some or all of the curable component of the switchable adhesive composition of the present invention may be provided by way of curable moieties that are bonded to the material or materials capable of undergoing cross-linking with isocyanate, e.g. a polyol as described above. In one embodiment, all of the curable component of the adhesive composition may be provided by means of such curable moieties ("fully bound-in").

As mentioned above, according to alternative definitions of the present invention, the finished adhesive composition should contain at least 0.01 equivalent of double bonds per kg (mol/kg), preferably at least 0.05 eqv/kg, where fully bound-in curable moieties are used; at least 0.05 eqv/kg of double bonds, preferably at least 0.15 eqv/kg where partially bound-in curable molecules are used; and at least 0.15 eqv/kg, preferably at least 0.4 eqv/kg, of double bonds when the curable molecules are simply mixed in to the adhesive composition. This may provide a more useful guide to the amount of curable molecules or curable moieties to be included in the adhesive composition than the actual proportions by weight, which are dependent upon the molecular weight of the curable molecules/moieties and other components of the composition.

Suitably, for fully bound-in curable moieties, the composition may comprise up to about 0.15 double bond equivalents per kilogram. For partially bound-in curable molecules, the composition may comprise up to about 0.3 eqv/kg. and for mixed-in curable molecules, the composition may comprise up to about 0.5 eqv/kg.

Where one or more mixed-in curable molecules are used, the adhesive composition of the invention may comprise at least about 10% wt. curable molecules, preferably about 30-40% wt., as mentioned below.

Where one or more partially bound-in curable molecules are used, the adhesive composition of the invention may comprise at least about 5% wt. curable molecules, preferably about 20-30% wt.

Where fully bound-in curable moieties are used, the adhesive composition suitably comprises at least 1-1.5% wt. curable moieties to achieve a practical switchable adhesive, although as little as 0.1% wt. may be sufficient for some applications. In some embodiments, the adhesive composition may comprise at least 0.5-1.5% wt. curable moieties. The proportion by weight of the curable molecule or moieties in the adhesive composition as a whole is a function of the molecular weight of the curable molecule or moieties. Suitably at least 20% of the available functional groups comprising an active hydrogen atom in the material or materials capable of undergoing cross-linking with isocyanate other than by free radical polymerisation such, for example, as the polyols described above, may be bonded to curable moieties. In some embodiments, at least 50% of the available functional groups containing an active hydrogen atom may be bonded to curable moieties. It is preferred that at least 30% of the functional groups containing an active hydrogen atom should remain available for cross-linking with the isocyanate. In the case of a small curable moiety such as isocyanatoethyl methacrylate, bonding of the curable moiety to about 50% of the functional groups containing an active hydrogen atoms corresponds to a weight proportion of curable moieties in the final composition of about 4% wt.

In the broadest sense, any conventional known unsaturated compounds or moieties that are curable by free radical polymerisation could be used as the curable molecules or curable moieties, but preferred examples, used alone or in mixtures, are curable molecules or moieties such as acrylic acid esters or methacrylic acid esters of alcohols, glycols, pentaerythritol, trimethylpropane, glycerol, aliphatic epoxides, aromatic epoxides including bisphenol A epoxides, aliphatic urethanes, aromatic urethanes silicones, polyesters and polyethers, as well as ethoxylated or propoxylated species thereof.

Most effective are curable molecules and curable moieties having more than one unsaturated site, i.e., greater than single functionality, such as a functionality of 2 or 3 or higher. Multiple functionalities of 4 or more are especially effective because curable molecules and moieties of this type are able to form highly cross-linked three-dimensional polymeric networks which are an important feature of switching, as will be explained below. Also, many curable molecules having multiple functionalities are commonly available at reasonable cost.

For medical applications where contact with skin occurs, curable molecules used in the switchable adhesive composition preferably have a molecular mass greater than 500 dalton, more preferably greater than 1000 dalton and most preferably greater than 1500 dalton. Molecules of this size are generally understood to be incapable of being absorbed easily through the skin and hence are less hazardous. Alternatively, fully bound-in curable moieties may be employed.

Curable Molecules

Most preferably, the curable molecules are oligomers of at least one of the following formulae (I) to (V):

$$CA(BA)_nC \qquad (I)$$

where n is 0, 1, 2, 3 or 4,

A is a diisocyanate, a diepoxide, a diol or a dicarboxylic acid;

B is a diol when A is a diisocyanate or a dicarboxylic acid; B is a dicarboxylic acid when A is a diepoxide or a diol;

C is a hydroxyl containing acrylate ester when A is a diisocyanate or a dicarboxylic acid; C is an acrylic acid when A is a diepoxide or a diol;

$$C_2E(BCE)_nC_2 \qquad (II)$$

where n is 0, 1, 2, 3 or 4,

E is a tri-isocyanate, a triepoxide, a triol or a tricarboxylic acid;

B is a diol when E is a tri-isocyanate or a tricarboxylic acid; B is a dicarboxylic acid when E is a triepoxide or a triol;

C is a hydroxyl containing acrylate ester when E is a tri-isocyanate or a tricarboxylic acid; C is an acrylic acid when E is a triepoxide or a triol;

$$E_{(2n+1)}F_nC_{(3n+3)} \qquad (III)$$

where n is 0, 1, 2, 3 or 4,

E is a tri-isocyanate, a triepoxide, a triol or a tricarboxylic acid;

F is a triol when E is a tri-isocyanate or a tricarboxylic acid; F is a tricarboxylic acid when E is a triepoxide or a trial;

C is a hydroxyl containing acrylate ester when E is a tri-isocyanate or a tricarboxylic acid; C is an acrylic acid when E is a triepoxide or a triol;

$$G_{(n+1)}B_nC_{(2n+4)} \qquad (IV)$$

where n is 0, 1, 2, 3 or 4,

G is a tetra-isocyanate, a tetra-epoxide, a tetra-ol or a tetra-carboxylic acid;

B is a diol when G is a tetra-isocyanate or a tetra-carboxylic acid; B is a dicarboxylic acid when G is a tetra-epoxide or a tetra-ol;

C is a hydroxyl containing acrylate ester when G is a tetra-isocyanate or a tetra-carboxylic acid; C is a dicarboxylic acid when G is a tetra-epoxide or a tetra-ol;

$$DC_3 \qquad (V)$$

where D is a symmetrical isocyanurate trimeric ring structure or an asymmetric trimeric iminooxadiazinedione ring structure consisting of three diisocyanate molecules, or a linear trimeric biuret or allophanate structure, C is a hydroxyl containing acrylate ester;

and wherein the oligomers have a weight average molecular weight of at least 500 dalton, for example in the range 500 to 10,000 dalton.

A major advantage of using such oligomers for medical applications of the switchable adhesive compositions according to the present invention is that, compared with known medical adhesives, biocompatible switchable medical adhesives can be produced exhibiting a zero in cytotoxicity tests complying with the methods described in ISO 10993-5 standard for the eluation test and also complying with the United States Pharmacopeia: <87> Biological Reactivity Tests, in vitro (Eluation Test).

Another advantage is that medium range molecular weight residuals (150-450 dalton or, in some cases, 150-900 dalton) in the produced adhesive compositions can be kept at very low concentrations. This is important because larger molecules are not able to penetrate the skin easily. Generally, skin penetration is believed to occur below around 500-1000 dalton, depending on the chemical nature of the molecule. For example, low polarity organic molecules may penetrate skin because their transport through skin is aided by skin grease (sebum).

The oligomeric curable molecules can be tailored to optimize the final switchable adhesive compositions for properties such as MVTR, viscosity, switching performance, adhesion, hydrophobic/hydrophilic balance, migration into and wrinkling of medical carrier films, etc.

The oligomers described above consist of a backbone molecule such as a polyether, a polyester, a polyurethane, a homopolymer of isocyanate, etc., with attached double bond curing groups.

The first step in synthesizing such an oligomer is to produce the backbone molecule (if a suitable candidate cannot be obtained from commercial sources) with pendant groups such as hydroxyl, epoxide, carboxylic acid, isocyanate, etc., so that the double bond curing molecule can be chemically bonded to the backbone molecule in a later stage. In general, any double bond curing molecule containing a suitable function in order to be attached to the backbone molecule could be used to form the pendant groups, but preferred species are hydroxyl containing acrylic esters and acrylic acids or hydroxyl containing methacrylic esters and methacrylic acids.

Preferred examples of chemical reactions that can be used to attach the double bond curing molecules to the backbone molecules are reactions between epoxides and acrylic acids, hydroxyl and acrylic acids, transesterification of acrylic acid to hydroxyl groups, isocyanate and hydroxyl containing acrylic esters. The most preferred of these examples is the reaction between isocyanate and hydroxyl containing acrylic esters.

In some embodiments, two (or more) different double bond curing molecules may be used; one of higher molecular weight than the other. The higher molecular weight double bond curing molecule may be reacted with the backbone molecule in a first step, followed by addition of the lower molecular weight double bond curing molecule. In general, higher molecular weight double bond curing molecules are preferred for medical applications, for the reasons given above, but unreacted residual lower molecular weight molecules may be easier to remove. Accordingly, excess isocyanate (for example) may first be reacted with a relatively high molecular weight hydroxyl containing acrylate ester to ensure that substantially all of the hydroxyl containing acrylate ester is reacted, and the excess isocyanate is then reacted with relatively low molecular weight hydroxyl containing acrylate ester. Residual low molecular weight hydroxyl containing acrylate ester may then be removed, e.g., by evaporation.

In principle, each of the needed reactive functions can be situated either on the backbone molecule or on the double bond curing molecule but, most commonly, epoxides and isocyanate functions are provided on the backbone molecule, while the hydroxyl function is usually attached to the backbone molecule in the case of an ester forming reaction or is usually attached on the double bond curing molecule in the case of a urethane forming reaction.

Oligomer Specifications for Medical Applications

Residuals of molecules below 450 dalton or more preferably 900 dalton should be kept at concentrations below 3 w/w % or more preferably below 1 w/w %. This ensures that the number of low molecular weight species is minimised. It does not necessarily apply to residual molecules of less than approximately 200 dalton because these will generally be evaporated during drying steps in the manufacturing process when the switchable adhesive composition is coated on a substrate and dried at elevated temperature.

Preferred is methacrylic acid or its different hydroxyl containing esters, since methacrylated oligomers are in general less toxic and allergenic than their acrylate counterparts.

Preferred hydroxyl containing acrylic esters are hydroxyl ethylmethacrylate or propoxylated methacrylic acid esters having an average of 1-6 or 1-10 propylene glycol units. Alternatively their ethylene glycol counterparts can be used but this is usually less beneficial when more than two ethylene glycol units (but suitably n<3) are used because that they contribute to a more hydrophilic oligomer of slightly lower molecular weight and higher viscosity.

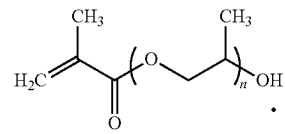

where n is 1-6 or 1-10

Examples of other hydroxyl containing acrylic esters are hydroxyl (CH2)n methacrylic esters where n is 4-8, caprolactone methacrylate, 3-(Acryloyloxy)-2-hydroxypropyl methacrylate and glycerol dimethacrylate.

In order to produce an adhesive with satisfactory switching performance (reduction in peel force, switching time), where the curable molecules are mixed-in the adhesive composition, the pure oligomer should contain at least 1 equivalent of double bonds per kg (mol/kg) but preferred are oligomers with more than 1.5 or 2 double bond equivalents per kg.

To avoid migration into and swelling of common medical polymeric films used as carrier films or release layers, the oligomer needs to have a weight average molecular weight, Mw, of at least 500 dalton, more preferably at least 1500 dalton, combined with a very low amount of molecules below 400 dalton or more preferably below 900. In addition, the hydrophobic/hydrophilic balance of the oligomer should be different from that of the medical polymeric film.

Preferably, the oligomer has an average number of curable functions per molecule of 2 or more. Multiple functionalities of 2 or more, for example 3 or more, or functionalities of 4 or more, are especially effective because oligomeric curable molecules of this type are able to form highly cross-linked three-dimensional polymeric networks which are an important feature in transforming the adhesive compositions of the invention from a tacky state to a non-tacky or low-tack state and from a viscoelastic state to an elastic state.

If the Mw of the oligomer is increased, it is important to increase the number of curable functions per molecule in order to conserve the equivalent number of double bonds per kg.

In order to ensure low cytotoxicity, it is important to avoid oligomers that are too hydrophilic because they may be soluble in water to some degree and will therefore behave as more toxic towards the living cells used in the cytotoxicity test.

Preferred isocyanates are trimethyl hexamethylene diisocyanate, dicyclohexylmethane-4,4'-diisocyanate, isophorone diisocyanate, toluylene diisocyanate while more preferred are homopolymers of diisocyanate, e.g., allophanates, isocyanurates, iminooxadiazindiones, and biurets based on diisocyanates such as hexamethylene diisocyanate and isophorone diisocyanate.

Methods for Controlling Different Parameters
Moisture Vapour Transmission Rate (MVTR)

The moisture breathability of the adhesive composition can be improved by using more hydrophilic building blocks in the oligomer, e.g., by partly or completely exchanging diols such as polypropylene glycol or butanediol with polyethylene glycol. Similarly, hydroxyl containing esters such as mono or polypropylene glycol monomethacrylate can be partly or completely exchanged with mono or poly ethylene glycol methacrylate.

Switching Performance

The reactivity of the composition can be increased by using a higher number of curable groups/molecules in the oligomer or curable moiety and/or by using more reactive functionalities in the oligomer or curable moiety, e.g., partly or completely exchanging methacrylate with acrylate (acrylates are more reactive but also slightly more toxic) and/or by using a higher proportion of oligomeric curable molecules or curable moieties in the adhesive composition.

Viscosity of the Pure Oligomer

The interactions between oligomer molecules and thereby the viscosity of the oligomer can be decreased by using bulky groups (e.g., by adding methyl groups or by branching of the molecular chain) and/or introducing asymmetry or higher hydrophobicity in the oligomer molecules e.g., by exchanging hexamethylene diisocyanate with trimethylhexamethylene diisocyanate, exchanging isocyanurate with iminooxadiazinedione, exchanging butanediol with methylpentandiol, exchanging polyethylene glycol with polypropylene glycol, etc.

Adhesion

This parameter can be regulated by the polarity or viscoelastic properties of the oligomer.

Hydrophobic/Hydrophilic Balance

See MVTR.

Migration

Diffusion of the oligomer into the medical film used as a carrier layer or release liner is governed by the size of the molecules and their solubility in the films.

Examples of Oligomer Backbone Molecules with Suitable Pendant Functions

Polyethers are usually propoxylated/ethoxylated bisphenol A, alkyl diol, alkyltriol, as well as mono-, di- or higher trimethylolpropane or pentaerythritol.

Polyesters end capped with hydroxyl groups are produced by reacting dicarboxylic acids with a slight excess of a diol. If a higher number than 2 acrylate functions is needed, polyols like trimethylolpropane or pentaerythritol could be included as well as curable unsaturated diacids such as itaconic, fumaric and maleic acid.

Backbone molecules with pendant epoxy groups can be produced, for example, by reacting an excess of di-epoxides with saturated or unsaturated diacids (in a similar fashion to diol and diisocyanate to result in the products A, ABA, ABABA etc).

Adhesive Compositions

The switchable adhesive composition according to the invention may comprise a mixture, in proportions by weight, of up to to 99.89% of a polyurethane adhesive component, an amount up to 85% of at least one mixed-in or partially bound-in oligomeric curable molecule or fully bound-in curable moiety that is curable by free radical polymerization, 0.1% to 10% of photoinitiator, and 0.01% to 2% of stabiliser, the balance being incidental constituents.

Where a mixed-in or partially bound-in oligomeric curable molecule is employed, the adhesive component and the oligomeric curable molecule are preferably mutually soluble when dry, although good results may be obtained when the oligomeric curable molecule is uniformly dispersed in the adhesive component, said adhesive component and oligomeric curable molecule being mutually insoluble or only partly mutually soluble when dry.

Preferably, the amount of the adhesive component present in the mixture is in the range 20% to 90% by weight, more preferably 20% to 75% by weight or 40% to 80% by weight, more preferably 50% to 70% by weight.

Preferably, the proportion of mixed-in or partially bound-in oligomeric curable molecules in the mixture ranges from 10% to 80% by weight, more preferably 20% to 75% by weight, more preferably 20% to 60% by weight, more preferably 30% to 50% by weight.

Preferably, the photoinitiator is present in the mixture in the proportions 0.05% to 5% by weight, more preferably 0.1% to 2% by weight, more preferably 0.1% to 1% by weight or 0.5% to 1% by weight.

Preferably, the photoinitiator is also soluble in the adhesive component and oligomeric curable molecules, although it will be capable of exerting its curing initiating effect upon exposure to an activating light source if finely dispersed through the dry mixture but not dissolved in it.

As mentioned above, in some embodiments of the switchable adhesive composition, at least some of the oligomeric curable molecules may be bound-in to the adhesive component.

In some embodiments of the switchable adhesive composition, curable moieties may be fully bound-in to the adhesive component, optionally with no mixed-in or partially bound-in oligomeric curable molecules. In such compositions, the weight proportion of curable moieties, e.g. isocyanatoethyl methacrylate, may be as little as 2% to 3%, or even 0.2% to 0.3%, based on the total weight of the composition, but as mentioned above, proportions of at least 0.5% wt., 1.5% wt. or 3% wt. may be needed for some applications where a clear switch is required.

As with the curable oligomers that are mixed in or partially bound in to the adhesive component, as described above, in some embodiments, the curable moieties may have an average number of curable functions per moiety of 2 or more. Multiple functionalities of 2 or more, for example 3 or more, or functionalities of 4 or more, may be especially effective because curable moieties of this type are able to form highly cross-linked three-dimensional polymeric networks which are an important feature in transforming the adhesive compositions of the invention from a tacky state to a non-tacky or low-tack state and from a gel like state to an elastic state.

If the Mw of the curable moiety is increased, it may be important to increase the number of curable functions per moiety in order to conserve the equivalent number of double bonds per kg.

Preferred curable moieties are isocyanato $C_{1-6}$alkyl 2-$C_{0-6}$alkylacrylates, more preferably isocyanato $C_{1-3}$alkyl 2-$C_{0-3}$alkylacrylates such, for example, as isocyanatoethyl acrylate, isocyanatoethyl methacrylate, isocyanatoethyl 2-ethylacrylate, acrylic acid and methacrylic acid The adhesive composition may also contain a stabiliser which is added in order to prevent spontaneous reaction of the curable molecules during storage.

The weight proportion for the adhesive component is given above in terms of its dry weight and excludes any solvent which might be present in a commercially available bulk adhesive product.

In certain embodiments, the weight proportion of the adhesive component is from one of the following lower endpoints (inclusive), or to one of the following upper endpoints (inclusive). The lower endpoints are 10%, 20%, 30%, 40%, 50%, 60% and 70%; the upper endpoints are 99.89%, 99.79%, 95%, 90%, 85%, 80% and 75%.

In certain embodiments, the weight proportion of oligomeric curable molecules or curable moieties is from one of the following lower endpoints (inclusive), or to one of the following upper endpoints (inclusive). The lower endpoints are 5%, 10%, 15%, 20% and 25%; the upper endpoints are 85%, 80%, 70%, 60%, 50%, 40% and 30%.

As mentioned above, for fully bound-in curable moieties, in some embodiments a much lower proportion of curable moieties may be used that oligomeric curable molecules. This for curable moieties, the weight proportion is from one of the following lower endpoints (inclusive), or to one of the following upper endpoints (inclusive). The lower endpoints are 0.1%, 0.2%, 0.5%, 1%, 2%, 3%, 5%, 10%, 20% and 25%; the upper endpoints are 85%, 80%, 70%, 60%, 50%, 40%, 30%, 20%, 10%, 5%, 4%, In certain embodiments, the weight proportion of photoinitiator is from one of the following lower endpoints (inclusive), or from one of the following upper endpoints (inclusive). The lower endpoints are 0.05%, 0.1%, 0.2%, 0.5% and 1.0%; the upper endpoints are 10%, 5%, 4% and 3%.

The incidental constituents may be one or more of light scattering particles, fungicides, bactericides, colorants, humectants, tackifiers, etc.

Adhesive Composition Preparation Method

Preparation methods for the switchable adhesive compositions of the invention are very simple.

Mixture ("Mixed-in" Oligomeric Curable Molecules)

In the very simplest case, in which the composition is simply a mixture, the material cross-linkable with isocyanate, the oligomeric curable molecules, the photoinitiator and, if additional stabiliser is required over and above stabiliser that is added to the oligomeric curable molecules during their manufacture, the stabiliser are stirred together, in darkness or under red light conditions if a visible light photoinitiator is used or in absence of UV light if a UV photoinitiator is used, for about 30 to 60 minutes, most conveniently at room temperature. The curable molecules are usually solvent free, although some curable molecules of high viscosity may be carried in a solvent; the photoinitiator is usually solid and the most difficult component of the system to dissolve and/or disperse.

For ease of handling under laboratory conditions, up to 20% by weight of solvent can be added. For industrial scale preparation, solvent would preferably be omitted.

A UV switchable adhesive composition may be prepared as follows.

All components except for the isocyanate are loaded into a sealable glass jar and mixed to a homogenous solution using a magnetic stirrer over a period of approximately 60 minutes under protection from ultraviolet sources. In preparation for coating, the solution is vacuum boiled in order to remove all air bubbles present. Then, the isocyanate component is gently blended into the mixture taking care to avoid any new dispersal of air. After stirring the solution for approximately 30 minutes, or until it has reached a viscosity similar to syrup, the resulting adhesive solution is then spread onto a release liner using a spreader having a gauge of 150 μm and left to dry at room temperature for about 10 minutes.

The spread adhesive mixture is then further dried at 80-110° C. for 3 to 10 minutes. A slightly higher temperature and a longer drying time can be used if necessary. After drying, the thickness of the spread adhesive mixture will typically be about 60-80 μm.

A second carrier film is then applied to the other surface of the adhesive mixture.

Curable Molecules Partially Bound-in to Polyurethane Adhesive Component

Since an isocyanate component is used both in the cross linking of the polyol and in the synthesis of the oligomer, it is possible to use only a portion of the available isocyanate groups to cross link the polyol and to use the remaining isocyanates groups to react with the curable molecules, e.g. hydroxyl-containing acrylate ester. The benefit of this is that some of the curable molecules become chemically bound to the base polyurethane adhesive polymer and are therefore even less prone to exert toxicity to living cells.

In order to achieve this it is necessary to use an isocyanate with a functionality of 2 or more, preferably 3 or more, so that that at least a portion of the molecules has the necessary two or more isocyanate functions per molecule needed for creating a cross linked network with the polyol.

For example, if the starting material is a tri-functional isocyanate which is reacted with less than the stoichiometric equivalent amount of a hydroxyl-containing acrylate ester monomer the reaction products will, due to the random reaction behavior for this type of synthesis, be oligomers having 0 to 3 residual isocyanate groups per molecule.

The benefits of an adhesive produced according to the above procedure compared to the earlier described one containing only mixed in oligomers is:

A large proportion of the oligomer will be chemically bonded to the adhesive polymer backbone and therefore less able to exert toxicity.
 No residual hydroxyl-containing acrylate ester monomers in the finished adhesive since an excess of isocyanate is used in the production of the oligomer.
 A somewhat better release from the release liner for tackier versions.
 A 50% decrease in peel force on HDPE panels after switch compared to only mixed-in oligomers, despite a lower amount of curable functions. This is because the base adhesive polymer structure becomes, to a certain extent, intra-molecularly chemically bonded between different segments during the switch.
 Due to the lower amount of double bond carrying groups needed in order to switch the adhesive when the double bond carrying groups are bound-in, larger and therefore less toxic oligomers can be used.

Curable Moieties Fully Bound-in to Polyurethane Adhesive Component

Alternatively, curable isocyanate moieties may be fully bound into the polyurethane adhesive component, so that mixed-in or partially bound-in oligomeric curable molecules are not required. The material or materials capable of undergoing cross-linking with isocyanates forming part of the adhesive component of the adhesive composition of the invention may therefore comprise integral curable moieties as part of their molecular structure. For example, by using a monoisocyanate component with a pendant acrylate function or pendant acrylate functions, e.g. 2-isocyanatoethyl methacrylate, it is possible to chemically bond this to the hydroxyl functions (functional groups containing an active hydrogen atom) on the polyol that are not needed for crosslinking. In general a non-oligomeric monoisocyanate component with a pendant acrylate function or pendant acrylate functions may be used such, for example, as an isocyanato$C_{1-6}$alkyl acrylate or methacrylate. An isocyanate with an average of more than one isocyanate function may be added subsequently for cross-linking with the remaining hydroxyl groups on the polyol.

Alternative routes to bond a pendant curable moiety onto a polyol include transesterification or the reaction of the hydroxyl function with a double bond bearing anhydride such, for example, as itaconic acid anhydride, maleic acid anhydride or fumaric acid anhydride.

For medical applications, the benefit of this, as compared with embodiments in which only some oligomeric curable molecules are bound-in to the adhesive component, is that all of the acrylate groups are attached to the adhesive polymer matrix and are therefore much less able to exert any biological activity. A further advantage is that a significantly lower proportion of curable functions is needed, since the switch is more effectively achieved when different polymer segments are intra-molecularly chemically bonded during the switch as compared with when the segments are inter-molecularly cross linked.

Adhesive Medical Products

In another aspect of the present invention there is provided an adhesive medical product comprising a switchable adhesive composition in accordance with the invention. Said adhesive medical product may comprise a product selected from the group consisting of an adhesive dressing including an absorbent wound pad, a surgical incision drape, a bacterial barrier to covering a wound, the bacterial barrier having no absorbent wound pad, and a skin closure device for closing together the edges of a wound. Suitably, the adhesive medical product of the present invention may comprise a layer of the switchable adhesive composition of the invention disposed between a first carrier film and a second carrier film, wherein at least one of the carrier films includes a light occlusive layer on the surface of the carrier film remote from the adhesive composition.

The carrier films may have a low surface energy relative to skin so that the adhesive composition adheres preferentially to skin.

Differences Between First and Second Carrier Films

As noted above, preferably, one of the carrier films has a lower release force compared to the other. A difference in release force helps to enable the adhesive composition to remain in place on one of the carrier films whilst the other carrier film is removed so that the thus-exposed adhesive can be applied to skin. Differences in release force may be achieved, for example, by having one of the films siliconised or by using carrier films of different surface roughness; the adhesive composition will stick preferentially to the carrier film with greater surface roughness.

If it is intended that the adhesive composition should be easily removed from the skin after switching (i.e., the entire adhesive medical product is removed, including the adhesive), the surface of the carrier film may be left untreated.

On the other hand, if it is intended that the adhesive composition should remain on the skin after switching (e.g., a surgical incision drape, a bacterial barrier, a wound closure device), the surface of the carrier film next to the adhesive composition layer is treated with a coating of a silicone release agent. As a result, the surface of the carrier film has a low surface energy. By contrast, skin is not smooth (at a microscopic level) and has many surface irregularities, including pores. Hence, skin has an inherently high surface area as well as a high surface energy compared to the siliconised carrier film. Typical release forces for carrier films that are to be used as release liners when it is intended that the adhesive composition should remain on the skin after switching are given below, measured using Finat test method no. 10 and TESA 7475 tape of 25 mm width:

TABLE 1

Release force values for first and second release liners

| Release liner | Release levels (cN/25 mm) | Preferred range of release levels (cN/25 mm) |
|---|---|---|
| 1st (removed prior to skin application) | 1-50 | 1-15 |
| 2nd to be removed after curing | 50-2000 | 15-100 |

Carrier Film

Exemplary materials for the carrier film for carrying the switchable adhesive composition layer include polyethylene, polypropylene, polyurethane, ethylene/propylene copolymers, ethylene/ethylacrylate copolymers, ethylene/vinyl acetate copolymers, silicone elastomers, polydimethylsiloxanes, neoprene rubber, polyisobutylene, polyacrylates, chlorinated poly-ethylene, polyvinyl chloride, vinyl chloride-vinyl acetate copolymer, crosslinked polymethacrylate polymers (hydrogel), polyvinylidene chloride, poly (ethylene terephthalate), butyl rubber, epichlorohydrin rubbers, ethylenevinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoro-ethylene; and the like. More preferred are medical grade polyethers or polyester polyurethanes, thermoplastic polyester elastomer, perforated polyethylene, polypropylene and PET films, as well as medical grade woven or non-woven materials.

Photoinitiator

The photoinitiator may be any species which is capable of producing radical species under mild conditions, e.g., long wavelength UV (UVA, e.g., 300-400 nm) or visible light, in order to promote radical polymerization reactions in the curable molecules. As a consequence, when the photoinitiator becomes activated by exposure to long wavelength UV or visible light, the oligomeric curable molecules form chemical bonds with other oligomeric curable molecules and hence create polymeric cross-linking. In the embodiments of the switchable adhesive composition in which the constituents are brought together as a simple mixture, the effect of such cross-linking is to build a three-dimensional polymeric network entangling the adhesive polymer chains, thereby reducing their mobility and free volume. In embodiments in which at least some of the curable molecules are bound-in to the adhesive polymer constituent, there will be intra-molecular cross-linking.

Curable molecules having multiple functionality are able to form highly cross-linked three-dimensional polymeric networks easily.

Preferably, for medical applications, the UV exposure is under the mild conditions of long wave UV. The photoinitiator may alternatively produce radical species upon exposure to visible light, but products that are curable upon exposure to visible light require careful handling and/or require additional visible light occlusive layers to be incorporated in the product to avoid premature switching of the adhesive. The visible light occlusive layers need to be removed from the product at the appropriate time, when switching is desired.

Any conventionally known free radical initiators may be used. Particularly preferred are those initiators which react to long wavelength UV radiation, although initiators which react under visible light may be used. Examples of UV photoinitiators are: Benzoin and ethyl, isopropyl or isobutyl ethers of Benzoin; Benzophenone and hydroxy or methyl benzophenones; 2-Methyl-1[4-(methylthio)phenyl]-2-morpholinopropan-1-one; Acetophenone and 4'-Phenoxyacetophenone; Benzoyl-biphenyl; Benzil; Anisoin, as well as the Irgacures such as Irgacure 651 (benzyl dimethyl ketal), Irgacure 369 (2-Benzyl-2-dimethylamino-1-[4-morpholinophenyl]-butanone-1) or Irgacure 907 (2-methyl-1-[4-(methylthio)phenyl]-2-morpholino-propan-1-one); or the Uvatones, such as Uvatone 8302 (2,2-diethoxy-1,2-diphenyl ethanone).

Suitable free radical initiators for visible light activation include titanocene photoinitiators; dye/co-initiator systems, e.g., thionine/triethanol-amine; dye/borate salt systems; dye/peroxide systems and 1,2-diketone/co-initiator systems, e.g., camphor-quinone/tertiary amine. Examples of visible light photoinitiators are: Benzildimethyl ketal; Phenanthrenequinone; Titanocenes (of which Irgacure 784™ is one example, being an absorber of light in both the UV and the visible spectrum); Bis(2,4,6-trimethyl-benzoyl)-phenylphosphineoxide.

Stabiliser

The switchable adhesive composition may also contain a stabiliser, which is added in order to prevent spontaneous reaction of the curable molecules during storage. Examples of such stabilisers are hydroquinones such as Di-tert-butyl-4-methylphenol, or 1-Piperidinyloxy-4,4'-[1,10-dioxo-1,10-decanediyl) bis (oxy)]bis [2,2,6,6-tetra methyl] and Pentaerythritol tetrakis(3-(3,5-di-tert-butyl-4-hydroxyphenyl) propionate).

Optional Constituents

The switchable adhesive composition may also include photo-sensitisers. Since a sensitising species often absorbs energy in a different part of the spectrum from the initiator, more effective use of the light source may be achievable through the incorporation of sensitisers into the composition. Many photo-sensitisers are complex organic molecules, absorbing in the long wavelength UV and/or visible portion of the spectrum.

The switchable adhesive composition may also incorporate scattering particles to increase the effect of irradiation of the adhesive mixture by scattering the irradiating UV or visible light through the thickness of the adhesive mixture. Preferably, the light scattering particles are an inorganic compound such as silica powder, alumina powder, silica-alumina powder or mica powder with particle sizes of the order of 10 nm or greater, typically up to 1 μm.

The switchable adhesive composition may also include a component containing aliphatic thiol groups for reducing oxygen inhibition of the radical polymerization at the surface and preventing the surface from remaining tacky after cure when the surface is not protected by a film (second release liner). Apart from having oxygen-scavenging properties the aliphatic thiols can also take part in the radical polymerization of the curable molecules via thiol-ene reactions. For more effective contribution to the curing reaction a component with two or more thiol groups could be used, such as trimethylolpropanetris(3-mercaptopropionate) or pentaerythritoltetrakis(2-mercapto acetate). Amine synergists such as triethanol amine, ethyl-4-dimethylaminobenzoate or acrylated amines could also be used to reduce oxygen inhibition of the radical polymerization at the adhesive surface when this is not protected by a film.

Adhesive Wound Dressings

Adhesive wound dressings usually consist of an absorbent pad for absorbing exudates from the dressed wound, the absorbent pad being surrounded by an adhesive area for securing the wound pad in position over the wound. The adhesive area and the wound pad are supported on a carrier film which is often flesh coloured or of which may sometimes have an attractive design on its visible surface. The switchable adhesive compositions according to the present invention are ideal candidates for use as the adhesive in the adhesive area around the wound pad of an adhesive wound dressing.

Adhesive wound dressings are often applied by lay users in their own homes and are not necessarily apply by trained medical practitioners. Since few homes have access to suitable UV irradiation equipment, adhesive wound dressings incorporating the switchable adhesive composition according to the present invention are likely to be visible light actuatable rather than long wavelength UV actuatable.

For this reason, adhesive wound dressings intended for domestic use will preferably include light occlusive layers to prevent premature switching of the switchable adhesive composition, since premature switching would render the adhesive wound dressing ineffective because it would not stick to the skin sufficiently well and would peel from the skin too easily. The first light occlusive layer can form part of the release paper that is placed on the adhesive side of the dressing that is intended to be stuck to the skin. This first light occlusive layer is removed just before the adhesive wound dressing is applied over a wound. A second light occlusive layer is positioned on the opposite side of the adhesive wound dressing and remains in place until such time as the user wants to remove the adhesive wound dressing. At this point, the second light occlusive layer is removed, exposing the underlying switchable adhesive composition. Upon exposure to visible light, the switchable adhesive composition is transformed from its tacky state to a non-tacky or low-tack state. As a result, the peel force required to remove the adhesive wound dressing is reduced considerably and the dressing can be removed from the skin very easily.

On the other hand, adhesive wound dressings applied by trained medical practitioners may use a switchable adhesive composition that is actuatable by irradiation with long wavelength UV because trained medical practitioners are more likely to have access to a suitable UV lamp. In this case, light occlusive layers are not necessary. Instead, the upper surface of the adhesive wound dressing (i.e., the non-skin-contacting surface) only needs to be transparent or semitransparent to long wavelength UV light. When it is desired to remove the adhesive wound dressing, the trained medical practitioner shines a suitable UV light source over the adhesive wound dressing. As a result, the switchable adhesive composition is transformed from its tacky state to a non-tacky or low-tack state. As a result, the peel force required to remove the adhesive wound dressing is reduced considerably and the dressing can be removed from the skin very easily.

Surgical Incision Drapes

Although the occurrence of surgical site infections can vary from surgeon to surgeon, from hospital to hospital, from patient to patient, and also in accordance with the surgical procedure that is being conducted, it is believed that most surgical site infections are caused by the patient's own normal skin flora which enter the body through the surgical incision. The reason for this is that the patient's skin flora can move from the skin surface to the incision very easily. Also, innocuous bacterial flora on the patient's skin may also be host to pathogenic organisms.

Various surgical site infection countermeasures have been developed over the years to reduce the risk of such infections to patients. Obvious steps such as hygiene management of the operating room personnel and the operating room itself can lower the incidence of exogenous pathogens. Also, the scheduling of elective surgery so that it is conducted when patients have generally good health and hence concomitant healthy immune systems are also thought to be effective. Of course, not all surgery can be timetabled in this way and it is inevitable that many patients will have to undergo surgery when their health is far from perfect.

The application of bactericidal or antimicrobial agents to the patient's skin at the intended site of surgery has, in the past, been effective to kill bacteria. Various pre-operative skin preparation products, washes, surgical scrub tissues, wound cleaners, lotions and ointments have been used for many years for this purpose. However, with the emergence of bacteria that are resistant to antibiotic treatment, the effectiveness of such infection countermeasures is becoming lessened.

Longer lasting antimicrobial effects may be obtained by combining the antimicrobial agent applied pre-operatively with a surgical incision drape, for example in the form of a clear polymeric film with an adhesive backing on one side covered with a release liner. The release liner is removed and the surgical incision drape is placed over the intended site of incision, adhesive side down, and pressed into place on the patient's skin.

Unfortunately, known surgical drapes of this type can be lifted during surgery, which results in entry of bacteria into the surgical site. The lifting of the surgical drape is usually caused by failure of the adhesive to remain in contact with the patient's skin. Increasing the adhesive strength is not necessarily the ideal solution to this problem because more force is then required to remove the drape from the skin, which may result in damage of the skin near the surgical site.

As well as being switchable from a tacky state to a non-tacky or low-tack state upon exposure to long wavelength UV radiation or visible light, the switchable adhesive compositions of the present invention also undergo a change in their viscoelastic properties during switching. In the unswitched state, the adhesive compositions are viscoelastic and are able to flow into irregularities and pores, such as pores in a patient's skin surface. Good "wetting" occurs. In the switched state, the adhesive compositions are elastic and will move with a patient's skin. If required, they can be made to stay in position on a patient's skin, rather than being removed as described above in the discussion of adhesive wound dressings, by making the surface of the carrier film that supports the adhesive composition very slippery. In these circumstances, the switched adhesive remains preferentially attached to skin and is not removed when the supporting carrier film is removed.

This ability of switchable adhesive compositions according to the present to be made to adhere preferentially to the skin rather than to any carrier layer on which they are supported makes them suitable as surgical drapes.

Rather than using an adhesive as the medium to adhere a clear plastic film to the intended incision site, surgical incision drapes in accordance with the present invention use the adhesive itself as the material of the incision drape.

For use as a surgical incision drape, a medical skin covering is supplied as a layer of a switchable adhesive composition in accordance with the present invention sandwiched between two release liners. The release liners may include a light occlusive layer to prevent premature curing of the curable molecules of the switchable adhesive composition by exposure to incident light. Alternatively, the surgical incision drape may be packaged in a light occlusive covering that is removed before the surgical incision drape is deployed. The first release liner is removed just before the surgical incision drape is applied to the intended site of incision. Then the surgical incision drape is pressed on to the surface of the patient's skin at the intended site of incision, with the second release liner being uppermost and the adhesive composition layer being next to the patient's skin. The adhesive composition of the surgical incision drape is initially viscoelastic and is able to flow into irregularities and pores in the patient's skin surface and good "wetting" occurs. If necessary, any light occlusive layer on the second release liner is removed. Then the adhesive composition layer of the surgical incision drape is exposed to UV light or visible light through the second release liner to effect curing of the curable molecules in the adhesive composition.

The resultant cured adhesive composition layer is elastic, and therefore moves with the patient's skin, but it is no longer visco-elastic and cannot easily be removed from the skin. Removal of the second release liner after curing leaves the elastic adhesive composition in place as a thin layer on the patient's skin.

Preferably, the thin adhesive composition layer left in place on the patient's skin is transparent so that it is possible for the surgeon to see any markings that may have been made on the patient's skin before commencement of the surgical procedure. There is no wrinkling of the adhesive composition layer to obscure the surgeon's view of the incision site and the surgeon is able to make the incision through the cured elastic adhesive composition layer. Migration of the patient's normal skin flora, if not removed by pre-operative swabbing, is inhibited by the adhesive overlayer.

Towards the end of the surgical procedure, when the incision is to be closed, the cut edges of the skin are brought together and sutured, stapled or taped in the usual way through the switched adhesive composition layer that constitutes the surgical incision drape. Because of its adherence to the skin, the switched adhesive composition layer is difficult to peel away from the edges of the incision so is preferably left in position. Following closure of the incision, an area around the site of the incision may be cleared of the adhesive composition layer, although this is not necessary, to leave the incision site ready to receive a dressing.

Bacterial Barriers

A bacterial barrier may be applied to a wound sustained through injury. The wound site is first cleaned and disinfected before applying the bacterial barrier.

A bacterial barrier may also be applied to and incision site after surgery.

Such a bacterial barrier comprises a layer of a switchable adhesive composition in accordance with the present invention sandwiched between two release liners. The adhesive composition layer is initially viscoelastic prior to curing, but is transformable to an elastic state by curing of the curable molecules by exposure to UV or visible light. The release liners may include a light occlusive layer to prevent premature curing of the curable molecules of the adhesive composition by exposure to incident light. Alternatively, the bacterial barrier may be packaged in a light occlusive covering that is removed before the bacterial barrier is deployed. To apply the bacterial barrier to the closed incision site or over the wound, the first release liner is removed and the bacterial barrier is applied over the site of the closed incision or the wound, adhesive side down, pressing gently on the remaining release liner. The viscoelastic adhesive composition flows into the surface irregularities and pores of the patient's skin, including the edges of the incision or the edges of the wound. If necessary, any light occlusive layer on the second release liner is removed. The curable molecules in the adhesive composition layer are then caused to cure by exposure to UV light or visible light through the second release liner, causing the adhesive composition layer to change from its viscoelastic state to an elastic state. In the elastic state, the adhesive composition layer is no longer flowable, but is elastic so that it remains conformable with the patient's skin over the closed incision site, as the patient moves about.

The second release liner is removed after the curing step and the patient "wears" the bacterial barrier in the form of a cured elastic adhesive composition layer. If required, a dressing may be placed over the bacterial barrier, for example to relieve direct pressure on the closed site of the incision or wound.

Any bacteria remaining on the patient's skin prior to applying the bacterial barrier become immobilised in the cured adhesive composition layer and cannot migrate into the closed incision site or wound. The cured adhesive composition layer is breathable and allows moisture to escape from the pores of the patient's skin. Good wound healing is promoted by this breathability and by the exclusion of bacteria. The bacterial barrier eventually sloughs away with the shedding of skin cells from the surface of the patient's skin as wound healing progresses.

When the wound has healed sufficiently to permit removal of any sutures or staples, these can be removed without requiring the bacterial barrier to be removed beforehand. Rather, the sutures or staples can be removed through the bacterial barrier that remains if it has not already fallen away with the patient's dead skin cells.

Skin Closure

In a further aspect, the present invention may find use in skin closure applications.

In recent times, cyanoacrylate adhesives have found widespread use as an alternative to the traditional methods of suturing and/or stapling and/or taping for closing wounds. Such cyanoacrylate adhesives are fast and relatively simple to use; they are also comfortable for the patient to wear. They form an effective bacterial barrier and, from the physician's point of view, there is no risk of needle sticks. Finally, there is no need for a second visit to the physician for removal of the cyanoacrylate adhesive because it sloughs away with the patient's dead skin cells as wound healing progresses.

However, there are a number of disadvantages to using such cyanoacrylate adhesives in a skin closure application. Firstly, they give rise to toxic vapours when applied and during the cure; they undergo a pronounced exothermic reaction when curing, resulting in a burning sensation on the patient's skin. There is also a risk of scarring from adhesive flowing into the wound and, for wounds close to the eye, a risk of the adhesive entering into the patient's eye and sticking the eyelids together and/or sticking the eyelids to the eyeball. The curing speeds of cyanoacrylate adhesives depend on the formulation, but as curing is triggered by moisture, they can cure very rapidly on the patient's skin as a result of the moisture present at the skin surface. Sometimes, curing is too rapid and occurs before the edges of the wound have been properly brought together. Although simple to use in theory, mishandling of the cyanoacrylate adhesive as a skin closure medium can result in the adhesion of foreign objects to the wound, including the physician's fingertips or gloves.

The skin closure product using a switchable adhesive composition according to the present invention does not suffer from these drawbacks.

As with the surgical incision drape and bacterial barrier products described above, the skin closure product the present invention is most conveniently supplied as a layer of a switchable adhesive composition in accordance with the present invention sandwiched between two release liners. The release liners may include a light occlusive layer to prevent premature curing of the curable molecules of the adhesive composition by exposure to incident light. Alternatively, the skin closure product may be packaged in a light occlusive covering that is removed before the skin closure product is deployed. The curable molecules in the viscoelastic adhesive composition layer are curable to an elastic state by exposure to UV light or visible light.

In applying the skin closure product to a patient, the first release liner is removed and the skin closure product is placed on the patient's skin, adhesive side down, at one end of the wound to be closed. The physician uses the thumb and fingers of one hand to close together the edges of the skin of the wound and uses his other hand to press down the skin closure product progressively along and over the wound as the wound edges are progressively brought together.

When the skin closure product has been applied along the length of the wound, any light occlusive layer on the second release liner is removed. The curable molecules in the adhesive composition layer are then caused to cure by exposure to UV light or visible light through the second release liner. After curing, the second release liner is removed and a layer of the adhesive composition remains in place on the patient's skin. In its cured state, the adhesive composition layer is elastic and moves with the patient's skin, but has sufficient tensile strength to keep the edges of the wound together.

Curing of the curable molecules in the adhesive composition by radiation through the second release liner means that there is no risk of foreign objects becoming adhered to the wound and no risk of the physician's fingertips or gloves becoming adhered to the wound.

The cured adhesive composition layer is breathable and allows moisture to escape from the pores of the patient's skin. Moreover, the cured adhesive composition layer has good water resistance and does not require special care by the patient when bathing or showering.

The adhesive composition layer is gradually sloughed away with the patient's dead skin cells as wound healing progresses.

BRIEF DESCRIPTION OF THE DRAWINGS

The invention will be further described by way of example only and without limitation by reference to the drawings in which.

DETAILED DESCRIPTION OF THE DRAWINGS

First Embodiment

A first embodiment of an adhesive medical product using the switchable adhesive composition of the present invention will now be described with reference to FIGS. 1 to 5. The adhesive medical product in this example is an adhesive medical dressing.

Figure 1:
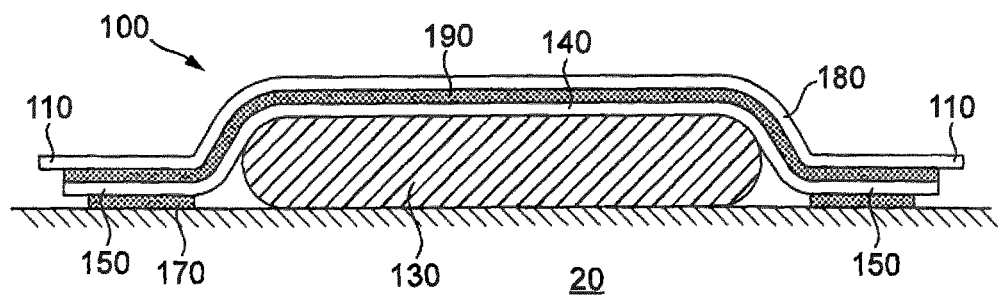
FIG. 1 is a cross-sectional view through an adhesive dressing in accordance with a first embodiment of the invention.

FIG. 1 is a cross-sectional view through an adhesive medical dressing 100 attached to a patient's skin 20. The adhesive medical dressing 100 is a multi-layer product having the following structure. The dressing 100 comprises a wound facing absorbent layer 130 disposed beneath a protective backing layer 140. At opposed edges 150, the backing layer 140 is provided with a switchable adhesive composition 170 which includes curable molecules that can be cross-linked under the influence of UV and/or visible light.

The backing layer 140 is provided with a light occlusive cover layer 180 which is releasably secured to the backing layer 140 by a weak adhesive 190. In an alternative arrangement, not shown here, the light occlusive cover layer 180 may be laminated to the backing layer 140. For ease of removal, the light occlusive cover layer 180 overlaps the backing layer 140 at its edges 110.

Since the adhesive composition 170 loses tackiness on exposure to visible and/or UV light, it is desirable that the adhesive 170 is not exposed to such light for a substantial period when the dressing 100 is applied to a patient. Thus, the adhesive composition 170 may be initially provided on the surface with release paper (see FIG. 3) which is preferably opaque to UV and visible light and which can be readily removed from the adhesive so that the dressing is ready for use when required.

Figure 2:
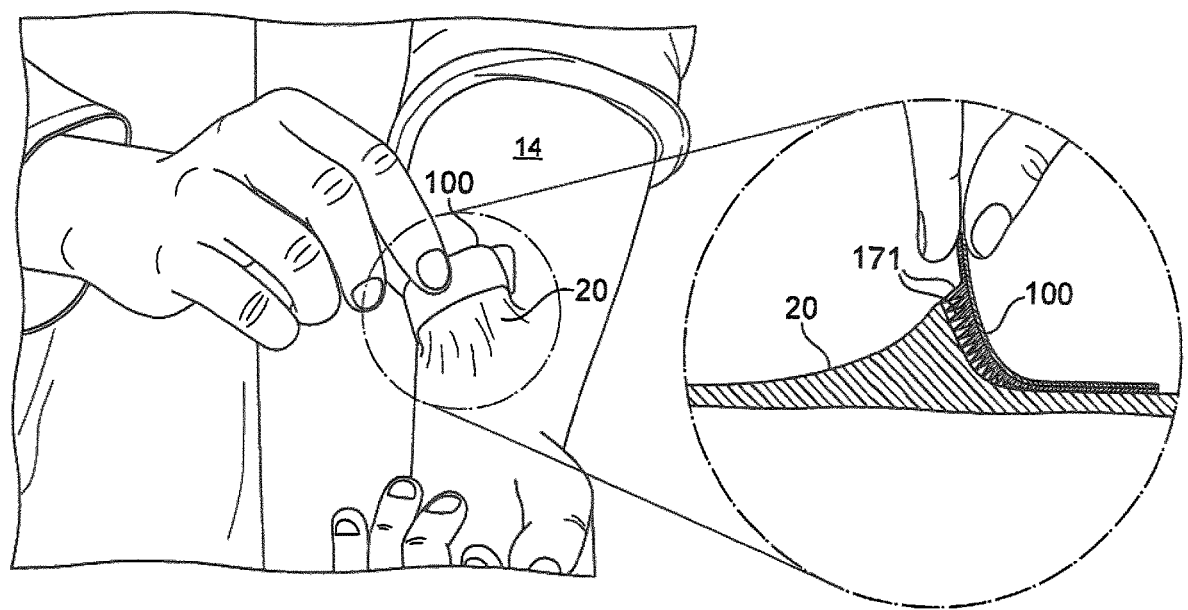
FIG. 2 is a perspective view showing the attempted removal from a patient's forearm of an adhesive dressing in accordance with the first embodiment of the invention and includes an enlargement bubble showing in partial cross-section how removal of the adhesive dressing causes the adhesive composition to extrude.

FIG. 2 is a perspective view showing the removal of an adhesive dressing 100 from the forearm 14 of a patient, prior to switching of the switchable adhesive composition. This may be done, for example, when the adhesive dressing 100 needs to be repositioned.

Before switching, the adhesive composition 170 is very tacky and sticks the adhesive dressing 100 to the patient's skin 20 quite firmly. Hence, when the patient attempts to peel the dressing 100 from his forearm 14 for repositioning, his skin 20 becomes stretched and the dressing 100 initially remains attached to the skin.

However, if the adhesive dressing 100 is peeled further from the skin, the adhesive layer 170 becomes extruded and forms "fingers" or "strings" 171 that extend between the stretched skin 20 and the backing layer 140. Because the surface properties of the backing layer 140 are selected to have a stronger affinity for the adhesive composition than a patient's skin, the adhesive detaches from the patient's skin and the adhesive layer 170 is re-formed.

Figure 3:
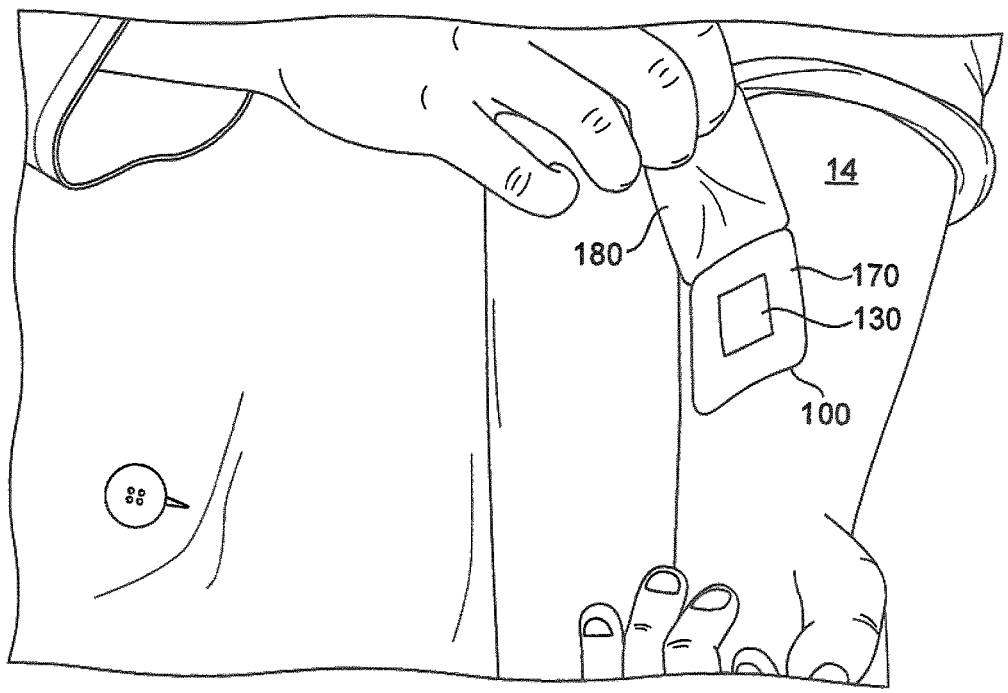
FIG. 3 is a perspective view showing removal of a light occlusive layer from the adhesive dressing in accordance with the first embodiment of the invention.

FIG. 3 is a perspective view showing the first step in preparing the adhesive dressing for removal by switching the adhesive composition to its non-tacky or low-tack state (as distinct from removal for repositioning purposes). FIG. 3 shows the patient removing the light occlusive cover layer 180 from the adhesive dressing 100 to expose the underlying adhesive composition layer 170. In this view, the wound pad 130 can also be seen.

The light occlusive cover layer 180 can be gripped at its edges 110 and peeled from the backing layer 140 to expose the underlying adhesive composition layer 170. Irradiation of the adhesive composition layer 170 with UV or visible light acts so as to generate free radicals that cause the curable molecules in the adhesive composition to undergo a curing reaction which, after a certain time (depending upon the adhesive composition mixture used), causes the adhesive composition 170 to lose its tackiness to such an extent that the dressing 100 can be removed very easily and without causing trauma to the patient.

In order that the removal of the light occlusive cover layer 180 does not itself cause trauma to the patient, the peel strength of the adhesive 190 adhering the light occlusive cover layer 180 to the backing layer 140 should be less than the peel strength of the adhesive 170 adhering the dressing 100 to the patient's skin 20.

Figure 4:
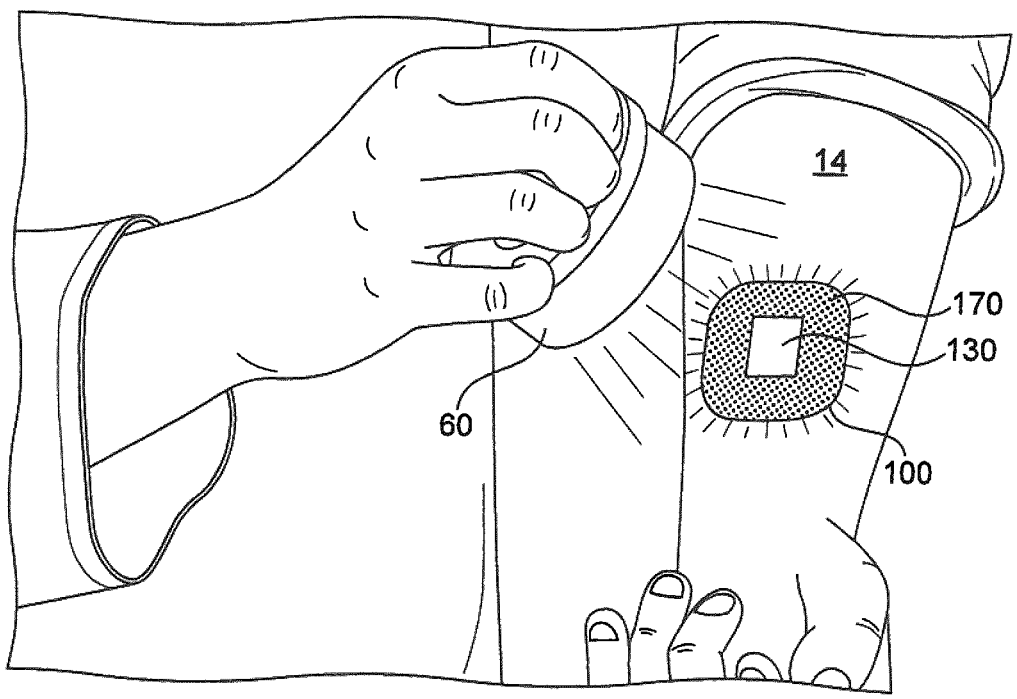
FIG. 4 is a perspective view showing the adhesive dressing in accordance with the first embodiment of the invention undergoing irradiation to effect switching of the adhesive.

FIG. 4 is a perspective view showing the adhesive dressing undergoing irradiation, in this example from a lamp 60, to effect cure of the curable molecules in the adhesive composition 170. The light from the lamp 60 (UV light or visible light, preferably long wavelength UV light) causes the photoinitiator in the adhesive composition 170 to generate free radicals that initiate curing of the curable molecules in the adhesive composition. Curing transforms (switches) the adhesive composition 170 from its tacky state to a non-tacky or low-tack state.

Figure 5:
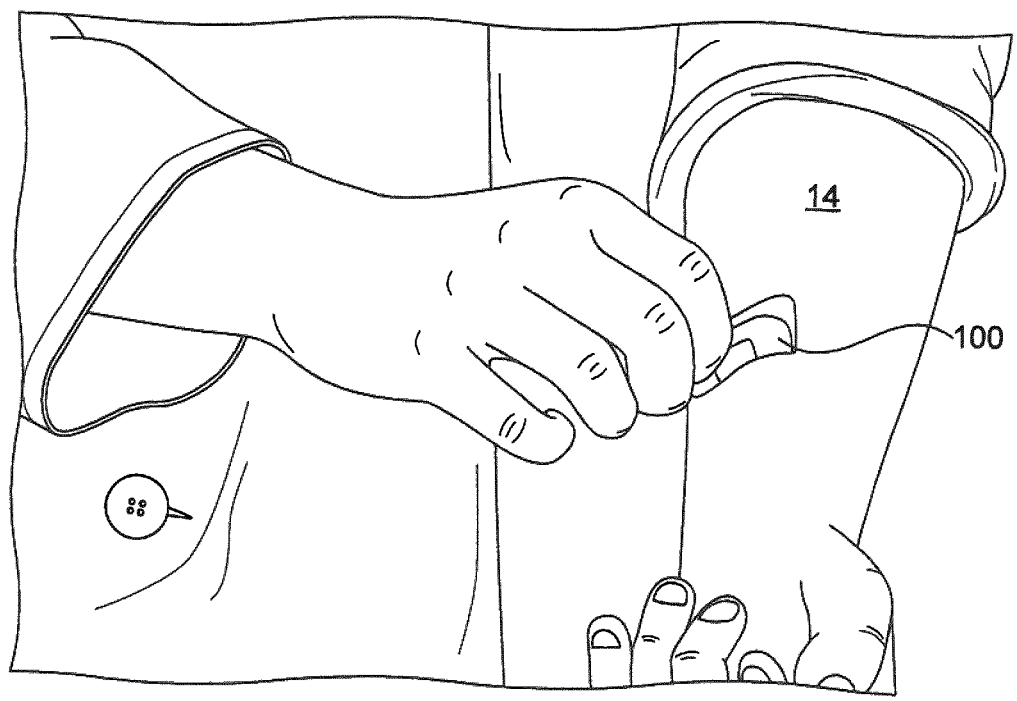
FIG. 5 is a perspective view showing how the adhesive dressing in accordance with the first embodiment of the invention may be easily removed after switching of the adhesive.

FIG. 5 is a perspective view showing how, after switching of the adhesive composition, the patient is easily able to remove adhesive dressing 100 from his forearm 14.

Second Embodiment

A second embodiment of an adhesive medical product using the switchable adhesive composition of the present invention will now be described with reference to FIGS. 6 to 11. The adhesive medical product in this example is a surgical incision drape.

Figure 6:
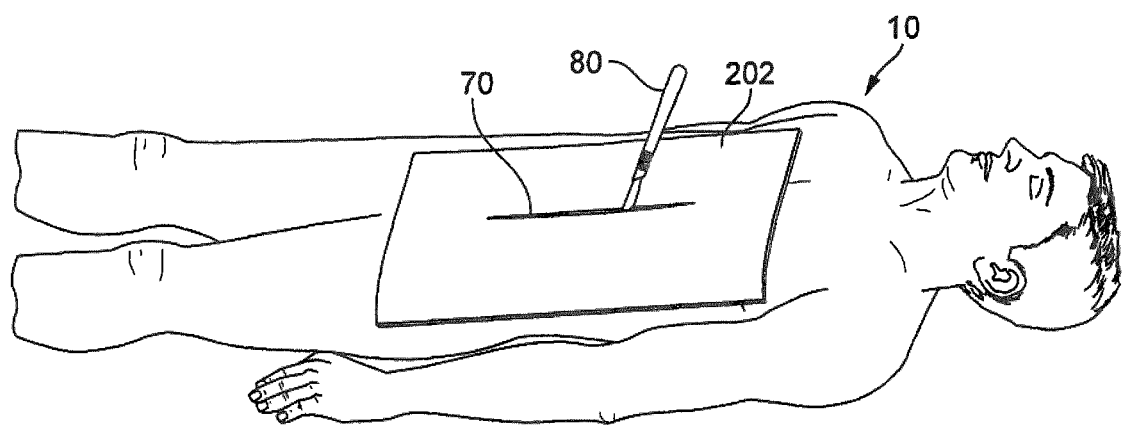
FIG. 6 is a perspective view showing an incision being made through a surgical incision drape according to a second embodiment of the present invention.

FIG. 6 is a perspective view showing a scalpel 80 making an incision 70 in the torso of a patient 10 through the adhesive layer 202 of a surgical incision drape in accordance with a second embodiment of the invention. The physician's hand holding the scalpel has been omitted from FIG. 6 for clarity.

Figure 7:
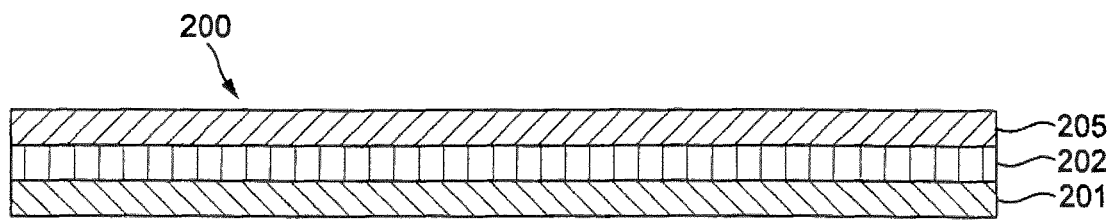
FIG. 7 is a cross-sectional view through the surgical incision drape in accordance with the second embodiment of the invention.

As shown in cross-sectional view in FIG. 7, the surgical incision drape 200 is a multiple layer article. The adhesive layer 202 is sandwiched between a first release liner 201 and a second release liner 205.

The first release liner 201 is a layer of siliconised plastic film, siliconised on the surface that faces the adhesive layer 202. In addition, the first release liner 201 is an occlusive material that prevents UV light and/or visible light passing through it and reaching the underlying adhesive layer 202.

The second release liner 205 is siliconised on the surface that faces the adhesive layer 202. Siliconised second release liner 205 is transparent to UV radiation and/or visible light. The siliconised second release liner 205 remains in place whilst the curable molecules in the adhesive layer 202 undergo curing by irradiation with UV light or by irradiation with visible light.

The occlusive first release liner 201 prevents inadvertent curing of the curable molecules in the adhesive layer 202 before the intended time by preventing the adhesive layer 202 from being exposed to UV light or visible light.

Figure 8:
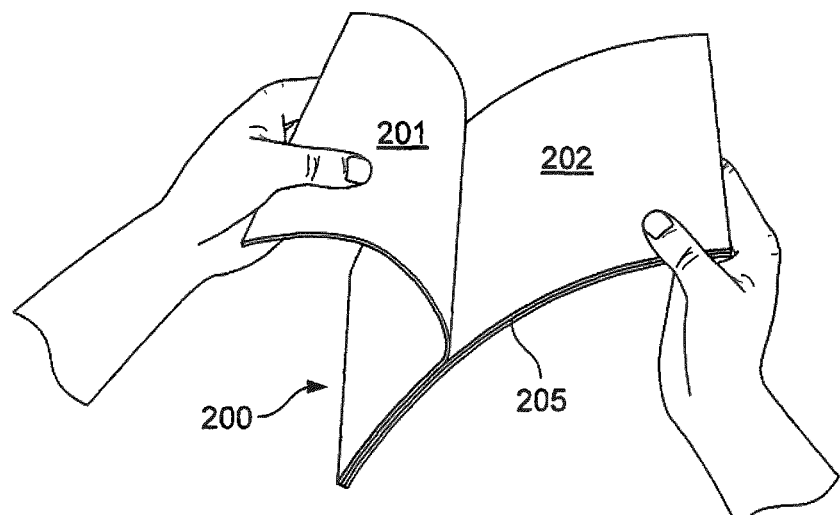
FIG. 8 is a perspective view showing the act of removal of one of the release liners of the surgical incision drape according to the second embodiment of the present invention.

FIG. 8 is a perspective view of the surgical incision drape 200 showing the removal of the first release liner 201 to expose the underlying adhesive layer 202. The second release liner 205 is still in place on the other side of the adhesive layer 202. After removal of the first release liner 201, the surgical incision drape 200 is quickly positioned over the site of the intended incision to minimise exposure of the adhesive layer 202 to any radiation that might bring about curing of the adhesive, and also to minimise exposure of the uncured adhesive to atmospheric oxygen. Positioning of the surgical drape is discussed in the next paragraph.

Figure 9:
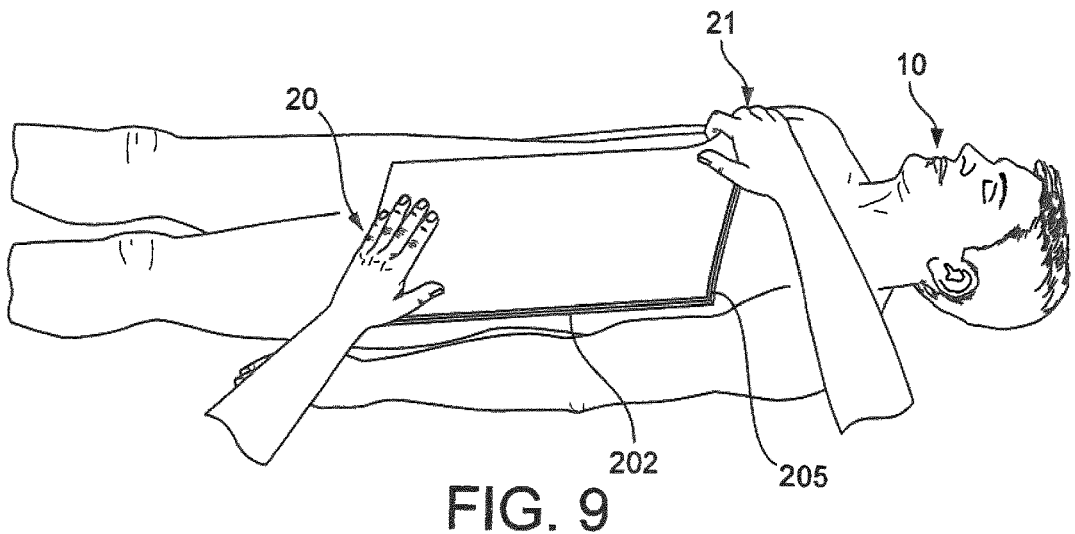
FIG. 9 is a perspective view of the surgical incision drape according to the second embodiment of the present invention in the act of being applied to the torso of a patient prior to surgery.

FIG. 9 is a perspective view showing the remaining layers of the surgical incision drape being applied to the torso of a patient 10 by the hands 20, 21 of a physician or nurse. In this view, the second release liner 205 is uppermost and the adhesive layer 202 is the layer that is brought into contact with the skin of the patient. The siliconised release surface of the second release liner 205 is next to the adhesive layer 202. Because the curable molecules of the adhesive composition of the adhesive layer 202 are uncured at this stage, the adhesive layer 202 is still in its viscoelastic state. In this state, the adhesive is able to flow into surface irregularities and pores of the skin to ensure intimate contact between the surgical incision drape and the patient's skin.

Figure 10:
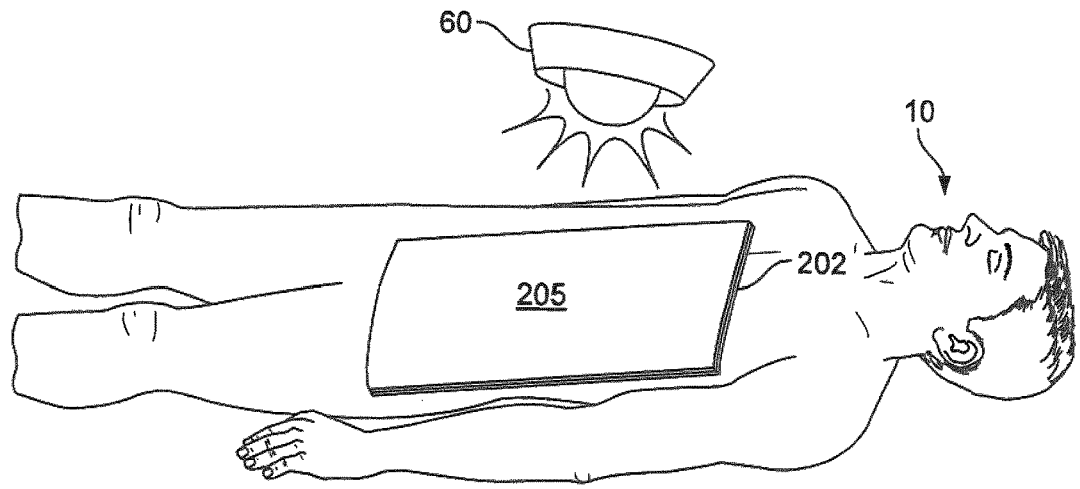
FIG. 10 is a perspective view of the surgical incision drape according to the second embodiment of the present invention in position on the torso of a patient and undergoing irradiation to effect cure of the adhesive.

FIG. 10 is a perspective view of the surgical incision drape in position on the torso of the patient 10 and undergoing irradiation, in this example from a lamp 60, to effect cure of the curable molecules in the adhesive composition of the adhesive layer 202. The light from the lamp 60 (UV light or visible light, preferably long wavelength UV light) passes through the transparent siliconised release liner 205 to the underlying adhesive layer 202 to initiate curing of the curable molecules in the adhesive composition. Curing transforms the adhesive composition layer from its viscoelastic state to an elastic state.

The transparent siliconised release liner 205 is retained in place over the adhesive layer 202 during the curing step to prevent oxygen in the ambient air from reacting with the adhesive composition as the curable molecules in the adhesive mixture undergo curing. Exposure to oxygen during curing causes the upper surface (i.e., the non skin contact surface) of the adhesive composition to remain slightly tacky after curing is complete. This slight tackiness is preferably avoided in a surgical incision drape because it may result in foreign objects (fluff, dust, etc.) becoming stuck to the surgical incision drape. Also, the slight tackiness may increase the possibility that parts of the surgical incision drape will be prematurely removed, for example by being abraded by contact with the physician's gloves. By retaining the siliconised release liner 205 in place over the adhesive layer 202 and curing the curable molecules in the adhesive layer 202 by irradiation through the siliconised release liner 205, the occurrence of surface tackiness in the cured adhesive composition layer is avoided.

Figure 11:
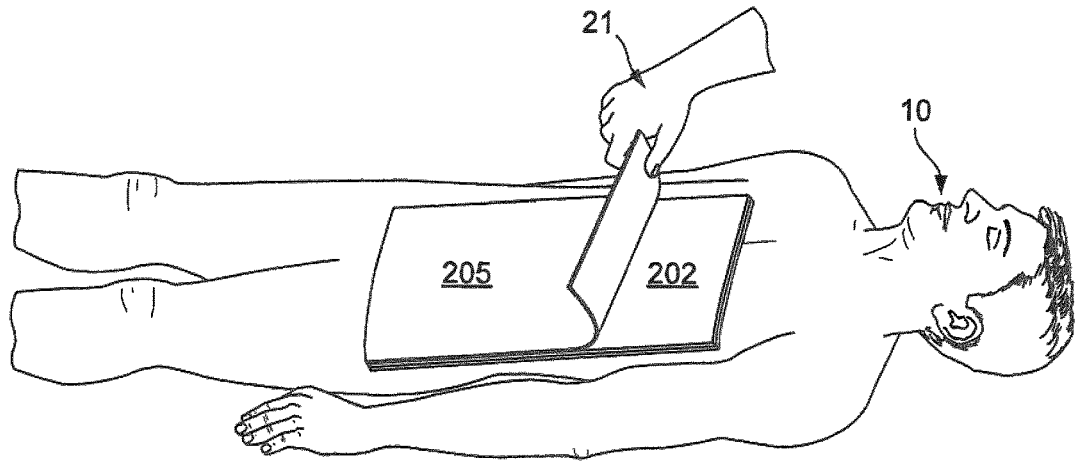
FIG. 11 is a perspective view showing the act of removal of the remaining layer of the second release liner of the surgical incision drape according to the second embodiment of the invention.

FIG. 11 is a perspective view showing the physician's hand 21 removing the siliconised release liner 205 from the adhesive layer 202 of the surgical incision drape after the curable molecules in the adhesive composition of the adhesive layer 202 have been cured. After removal of the siliconised release liner 205, only the cured adhesive composition layer 202 remains on the patient's skin.

Preferably, the cured adhesive composition layer is transparent so that the physician can see the site of the intended incision and any markings that may have been made on the patient's skin prior to commencement of the surgical procedure.

As mentioned above, in the cured state, the adhesive composition of the adhesive layer 202 is transformed from its initial viscoelastic state to an elastic state. In this state, the adhesive remains firmly stuck to the patient's skin but, by virtue of its elasticity, the adhesive layer is able to move with the patient's skin as the skin moves. Moreover, the cured adhesive layer is an effective barrier to bacteria. Any bacteria that remained on the surface of the patient's skin after the preliminary antibacterial swabbing step become immobilised in the cured adhesive layer and migration to the incision site is thereby inhibited.

Referring again to FIG. 6, the cured adhesive composition layer 202 of the surgical incision drape remains in position on the patient's skin and is incised, along with the patient's skin, when a physician (not depicted in FIG. 6) makes an incision 70 with a scalpel 80.

After surgery, the adhesive layer 202 at the edges of the incision may be peeled away so that the incision can be closed without interposition of any adhesive layer material between the mating skin edges. Closure of the incision may be performed in the usual way, for example by suturing or by means of surgical staples or surgical tapes. Alternatively, the adhesive composition layer 202 may be left in place during closure of the incision. If left in place, the adhesive composition layer 202 is gradually sloughed away with the shedding of skin cells from the surface of the patient's skin as healing takes place.

Third Embodiment

A third embodiment of an adhesive medical product using the switchable adhesive composition of the present invention will now be described with reference to FIGS. 12 to 17. The adhesive medical product in this example is a bacterial barrier, a type of wound covering that is similar to a dressing but having no absorbent wound pad.

Figure 12:
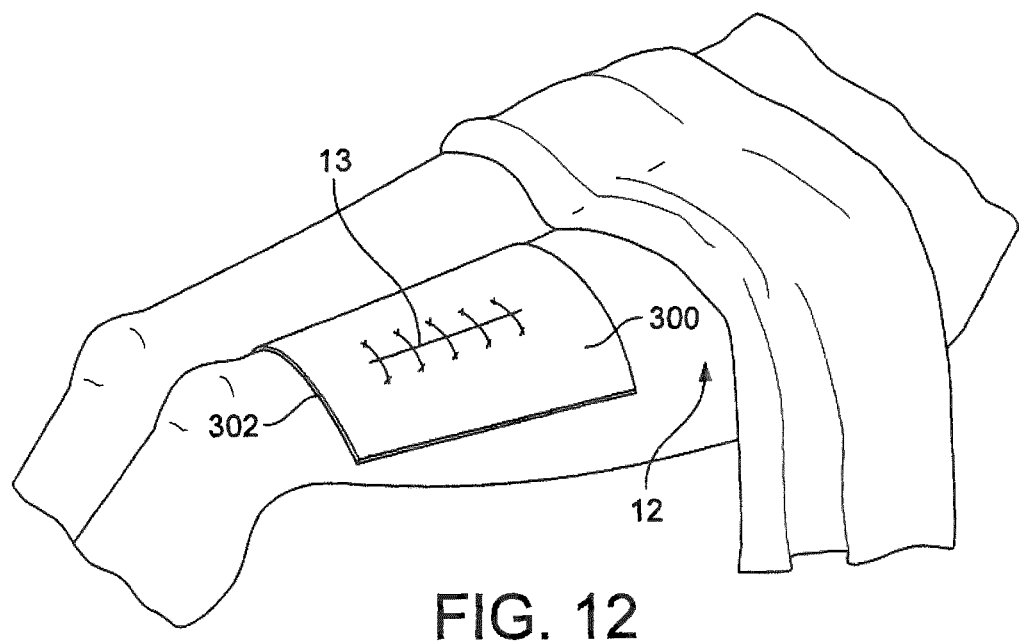
FIG. 12 is a perspective view of a bacterial barrier in accordance with a third embodiment of the present invention in place on a patient's thigh, overlying a sutured wound.

FIG. 12 is a perspective view showing a bacterial barrier 300 in accordance with the third embodiment of the invention in place on a patient's thigh 12, overlying a sutured wound 13. The bacterial barrier 300 in this view consists of a single layer 302 of cured adhesive composition, as will be explained in more detail below.

Figure 13:
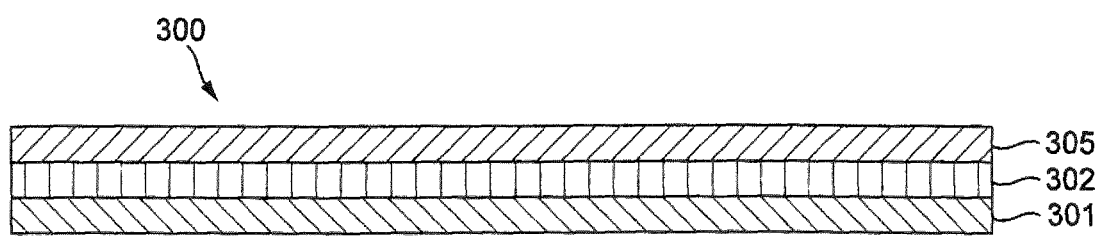
FIG. 13 is a cross-sectional view of the bacterial barrier in accordance with the third embodiment of the present invention.

As shown in cross-sectional view in FIG. 13, the bacterial barrier 300 is a multiple layer article. The adhesive layer 302 is sandwiched between a first release liner 301 and a second release liner 303.

The first release liner 301 is a layer of siliconised plastic film, siliconised on the surface that faces the adhesive layer 302. In addition, the first release liner 301 is an occlusive material that prevents UV light and/or visible light passing through it and reaching the underlying adhesive layer 302.

The second release liner 305 is also siliconised on the surface that faces the adhesive layer 302. Siliconised release liner 305 is transparent to UV radiation and visible light. The siliconised second release liner 305 remains in place whilst the curable molecules in the adhesive layer 302 undergo curing by irradiation with UV light or by irradiation with visible light.

The occlusive first release liner 301 prevents inadvertent curing of the curable molecules in the adhesive layer 302 before the intended time by preventing the adhesive layer 302 from being exposed to UV light or visible light.

Figure 14:
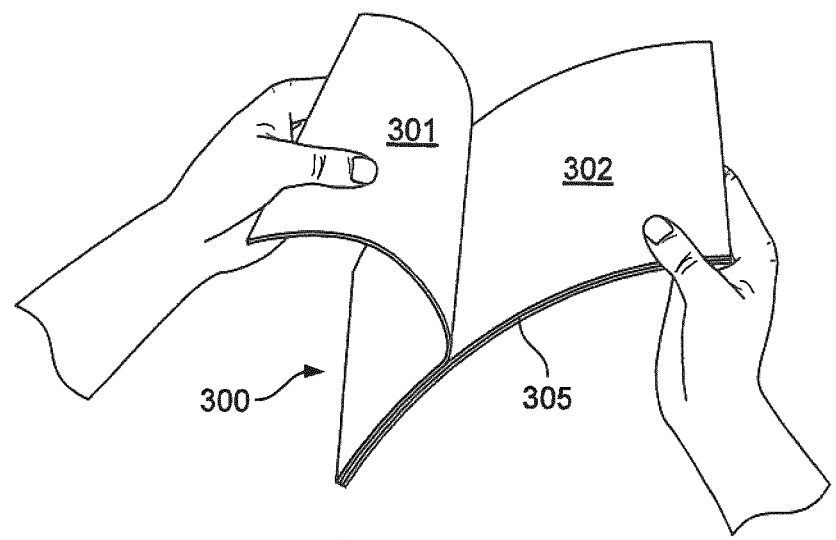
FIG. 14 is a perspective view showing the act of removal of the first release liner from the bacterial barrier according to the third embodiment of the invention.

FIG. 14 is a perspective view of the bacterial barrier 300 showing the removal of the first release liner 301 to expose the underlying adhesive layer 302. The second release liner 305, comprising its siliconised release surface, is still in place on the other side of the adhesive layer 302. After removal of the first release liner 301, the bacterial barrier 300 is quickly positioned over the site of the wound to be covered (see FIG. 12) so as to minimise exposure of the adhesive layer 302 to any radiation that might bring about curing of the curable molecules in the adhesive composition, and also to minimise exposure of the uncured adhesive composition layer to atmospheric oxygen. Positioning of the bacterial barrier is discussed in the next paragraph.

Figure 15:
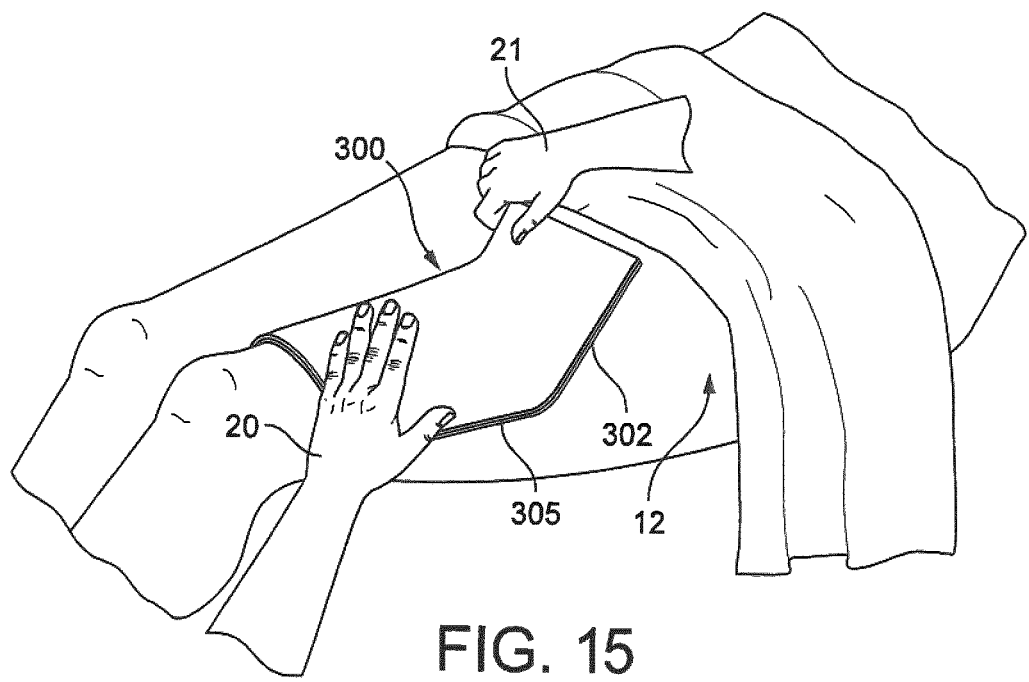
FIG. 15 is a perspective view of the bacterial barrier according to the third embodiment of the present invention being applied to the thigh of a patient to cover a sutured wound.

FIG. 15 is a perspective view showing the remaining layers of the bacterial barrier being applied to the thigh 12 of a patient by the hands 20, 21 of a nurse or physician. In this view, the second release liner 305 is uppermost and the adhesive layer 302 is the layer that is brought into contact with the skin of the patient. The siliconised release surface of the second release liner 305 is next to the adhesive layer 302. Because the curable molecules of the adhesive composition of the adhesive layer are uncured at this stage, the adhesive layer 302 is still in its viscoelastic state. In this state, the adhesive is able to flow into surface irregularities and pores of the skin to ensure intimate contact between the bacterial barrier in a surface and the patient's skin.

Figure 16:
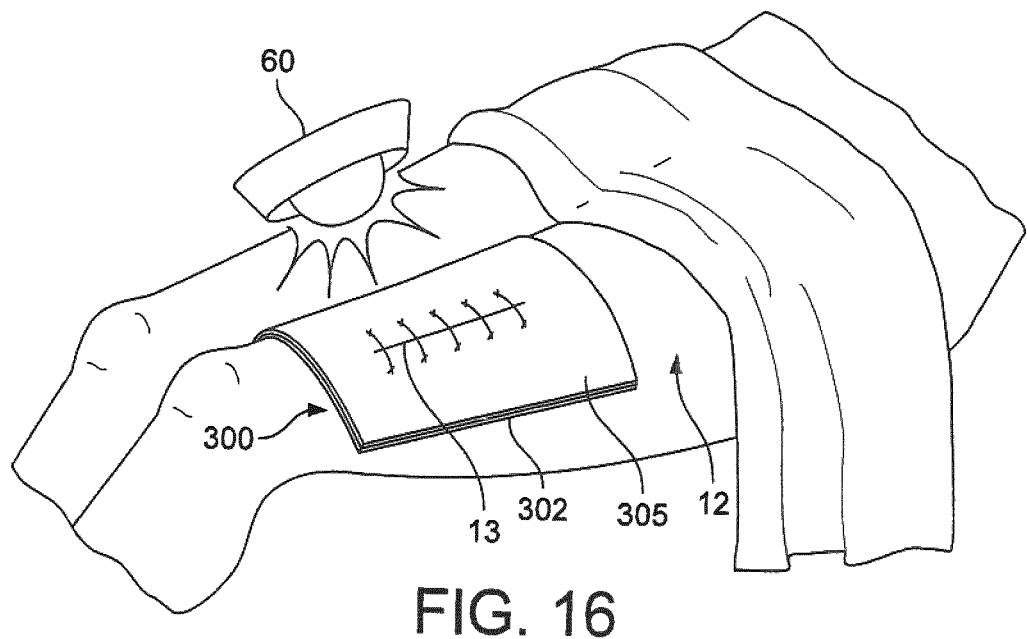
FIG. 16 is a perspective view of the bacterial barrier according to the third embodiment of the invention in position on a patient's thigh and in the act of being irradiated to cure the adhesive.

FIG. 16 is a perspective view of the bacterial barrier 300 in position on the thigh 12 of the patient and undergoing irradiation, in this example from a lamp 60, to effect cure of the curable molecules in the adhesive composition of the adhesive layer 302. The light from the lamp 60 (UV light or visible light, preferably long wavelength UV light) passes through the transparent siliconised second release liner 305 to the underlying adhesive layer 302 to initiate curing of the curable molecules in the adhesive composition. Curing transforms the adhesive composition layer from its viscoelastic state to an elastic state.

The transparent siliconised release liner 305 is retained in place over the adhesive layer 302 during the curing step to prevent oxygen in the ambient air from reacting with the adhesive composition as the curable molecules in the adhesive mixture undergo curing. Exposure to oxygen during curing causes the upper surface (i.e., the non skin contact surface) of the adhesive composition layer to remain slightly tacky after curing is complete. This slight tackiness is preferably avoided in a bacterial barrier because it may result in foreign objects (fluff, dust, etc.) becoming stuck to the bacterial barrier. Also, the slight tackiness may cause the bacterial barrier to be unintentionally removed, for example by being abraded by contact with the patient's clothes. By retaining the siliconised release liner 305 in place over the adhesive layer 302 and curing the curable molecules in the adhesive layer 302 by irradiation through the siliconised release liner 305, the occurrence of surface tackiness in the cured adhesive composition layer is avoided.

Figure 17:
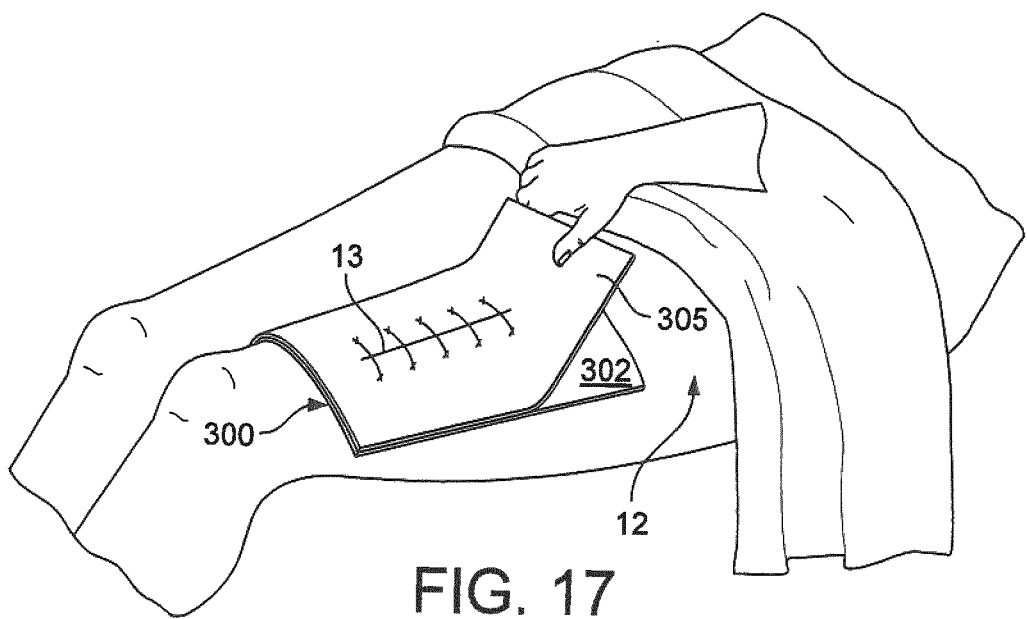
FIG. 17 is a perspective view showing the act of removal of the siliconised release layer of the bacterial barrier of the third embodiment of the invention, leaving just the cured adhesive layer in place on the patient's thigh.

FIG. 17 is a perspective view showing the physician's or nurse's hand 21 removing the siliconised second release liner 305 from the adhesive layer 302 of the bacterial barrier after the curable molecules in the adhesive composition of the adhesive layer 302 have been cured. After removal of the siliconised second release liner 305, only the cured adhesive composition layer 302 remains on the patient's thigh 12.

As mentioned above, in the cured state, the adhesive composition of the adhesive layer 302 is transformed from its initial viscoelastic state to an elastic state. In this state, the adhesive layer remains firmly stuck to the patient's skin but, by virtue of its elasticity, the adhesive layer is able to move with the patient's skin as the patient moves. The cured adhesive composition layer is an effective barrier to bacteria. Any bacteria that remained on the surface of the patient's skin after preliminary antibacterial swabbing become immobilised in the cured adhesive composition layer and migration to the site of the wound is thereby inhibited. The bacterial barrier is also a mechanical barrier against dirt and other foreign particles and substances.

Referring again to FIG. 12, the cured adhesive composition layer 302 of the bacterial barrier remains in position on the patient's skin over the wound 13. In practice, the wound 13 may be a wound that has arisen as a result of trauma to the patient or, as discussed above in relation to the second embodiment, the wound 13 may be the site of a surgeon's incision which has been sutured, stapled or taped closed after completion of the surgery.

The bacterial barrier is breathable and allows moisture to escape from the pores of the patient's skin. Moreover, the cured adhesive composition layer 302 has good water resistance and does not require special care by the patient when bathing or showering. Preferably, the cured adhesive composition layer 302 is transparent to allow inspection of the underlying skin surface without needing to remove the bacterial barrier.

The adhesive composition layer 302 is gradually sloughed away with the shedding of skin cells from the surface of the patient's skin as wound healing progresses.

Fourth Embodiment

A fourth embodiment of an adhesive medical product using the switchable adhesive composition of the present invention will now be described with reference to FIGS. 18 to 22. The adhesive medical product in this example is a skin closure film.

Figure 18:
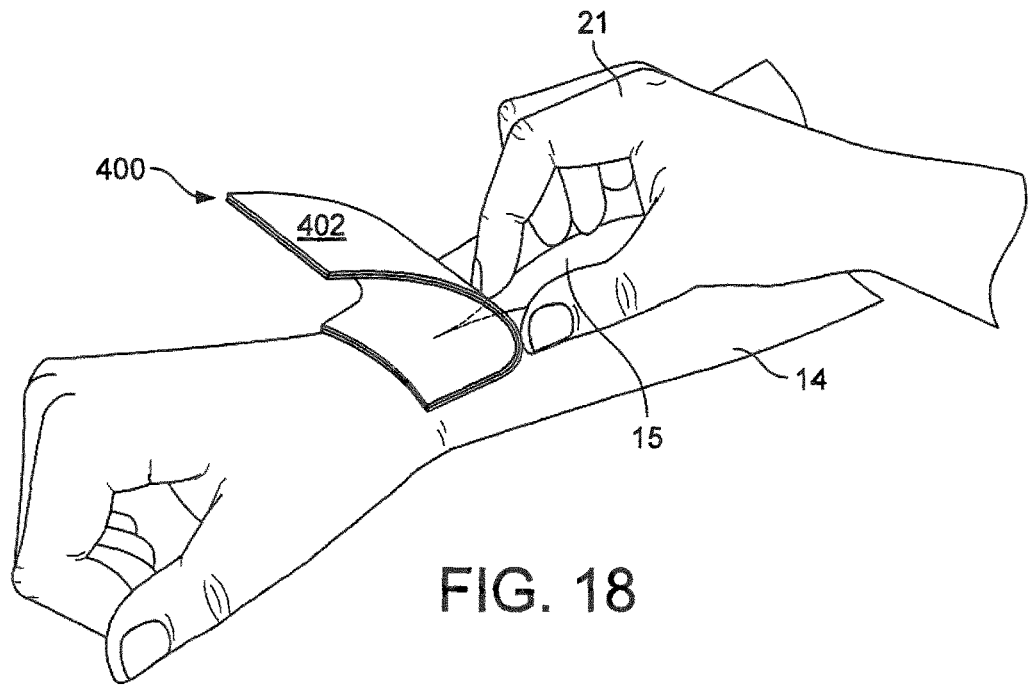
FIG. 18 is a perspective view showing a skin closure device according to a fourth embodiment of the invention in the act of being applied to a gaping wound on a patient's forearm as the skin edges are progressively brought together by a physician's thumb and fingers.

FIG. 18 is a perspective view showing a skin closure film 400 in accordance with the fourth embodiment of the invention being applied in place on a patient's forearm 14 for closing a gaping wound 15. The skin edges of the gaping wound 15 are shown being progressively urged together by the physician's or nurse's hand 21 as the skin closure film 400 is applied over the newly closed part of the wound 15. The second hand that the physician or nurse uses to apply the skin closure film 400 progressively to the newly closed part of the wound 15 is omitted from this view for reasons of clarity. The skin closure film 400 applied at this stage is a multiple layer product, as will be explained in more detail below.

Figure 19:
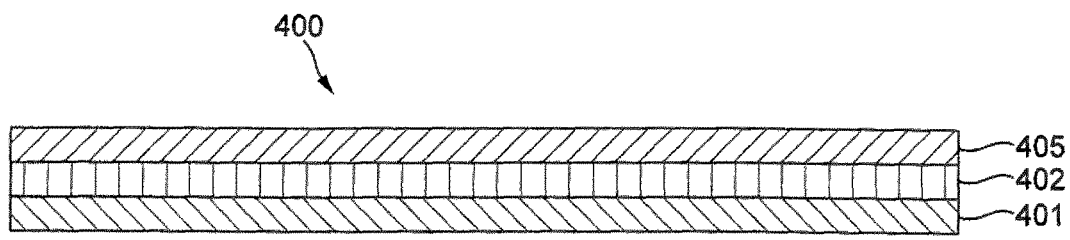
FIG. 19 is a cross-sectional view through the skin closure device in accordance with the fourth embodiment of the invention.

As shown in cross-sectional view in FIG. 19, the skin closure laminate 400 is a multiple layer article. The adhesive layer 400 is sandwiched between a first release liner 401 and a second release liner 405.

The first release liner 401 is a layer of siliconised plastic film, siliconised on the surface that faces the adhesive layer 402. In addition, the first release liner 401 is an occlusive material that prevents UV light and/or visible light passing through it and reaching the underlying adhesive layer 402.

The second release liner 405 is also siliconised on the surface that faces the adhesive layer 402. Siliconised release liner 405 is transparent to UV radiation and visible light.

The occlusive first release liner 401 prevents inadvertent curing of the curable molecules in the adhesive layer 402 before the intended time by preventing the adhesive layer 402 from being exposed to UV light or visible light.

Figure 20:
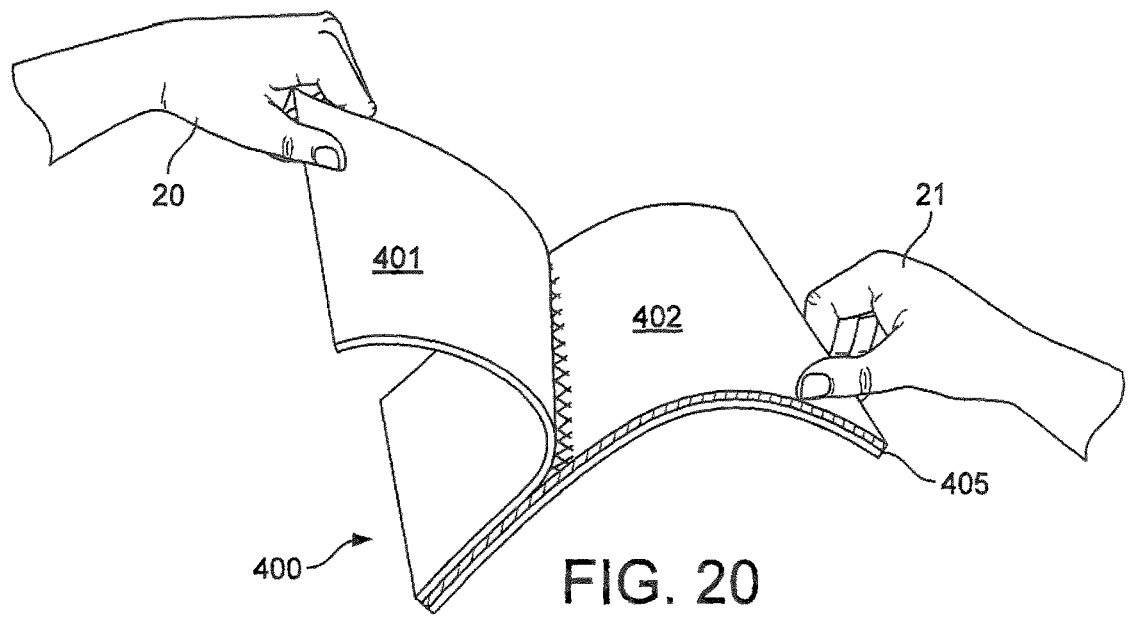
FIG. 20 is a perspective view showing the removal of the first release liner from the skin closure device in accordance with the fourth embodiment of the invention.

FIG. 20 is a perspective view of the skin closure laminate 400 showing the removal of the first release liner 401 to uncover the underlying adhesive layer 402. The second release liner 405 is still in place on the other side of the adhesive layer 402. After removal of the first release liner 401, the skin closure laminate 400 is preferably quickly positioned over the site of the wound to be closed (see FIG. 18) so as to minimise exposure of the adhesive layer 402 to any radiation that might bring about curing of the curable molecules in the adhesive, and also to minimise exposure of the uncured adhesive composition to atmospheric oxygen. Positioning of the skin closure laminate is discussed in the next paragraph.

Returning to FIG. 18, this is a perspective view showing the remaining layers of the skin closure laminate being applied to the forearm 14 of a patient by a nurse or physician. In this view, the second release liner 405 is uppermost and the adhesive layer 402 is the layer that is brought into contact with the skin of the patient. Because the curable molecules in the adhesive composition of the adhesive layer are uncured at this stage, the adhesive layer 402 is still in its gelled state. In this state, the adhesive is able to flow into surface irregularities and pores of the skin to ensure intimate contact between the skin closure film and the patient's skin.

The adhesive layer 402 is beneath the siliconised second release liner 405 and in contact with the skin of the patient's forearm 14. The second siliconised release layer 405 is transparent to UV light and/or visible light, for reasons which will be explained below.

Figure 21:
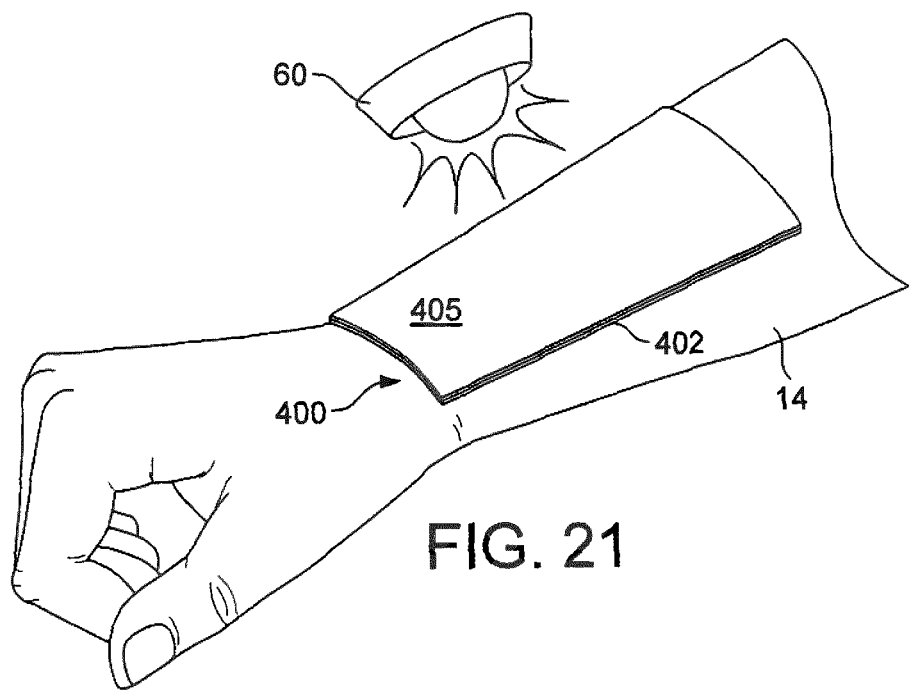
FIG. 21 is a perspective view of the skin closure device in accordance with the fourth embodiment of the invention in position on a patient's forearm and in the act of being irradiated to effect cure of the adhesive.

FIG. 21 is a perspective view of the skin closure laminate 400 in position on the forearm 14 of the patient and undergoing irradiation, in this example from a lamp 60, to effect cure of the curable molecules in the adhesive composition of the adhesive layer 402. The light from the lamp 60 (UV light or visible light—long wavelength UV is the preferred form of UV light) passes through the transparent siliconised release liner 405 to the underlying adhesive layer 402 to initiate curing of the curable molecules in the adhesive composition. Curing transforms the adhesive composition layer from its viscoelastic state to an elastic state.

The transparent siliconised release liner 405 is retained in place over the adhesive layer 402 during the curing step to prevent oxygen in the ambient air from reacting with the adhesive as the curable molecules in the adhesive mixture undergo curing. Exposure to oxygen during curing causes the upper surface (i.e., the non skin contact surface) of the adhesive composition layer 402 to remain slightly tacky after curing is complete. This slight tackiness is preferably avoided in a skin closure product because it may result in foreign objects (fluff, dust, etc.) becoming stuck to the skin closure film. Also, the slight tackiness may cause the skin closure film to be prematurely removed, for example by being abraded by contact with the patient's clothes. By retaining the siliconised release liner 405 in place over the adhesive layer 402 and curing the curable molecules in the adhesive layer 402 by irradiation through the siliconised release liner 405, the occurrence of surface tackiness in the cured adhesive composition layer is avoided.

Figure 22:
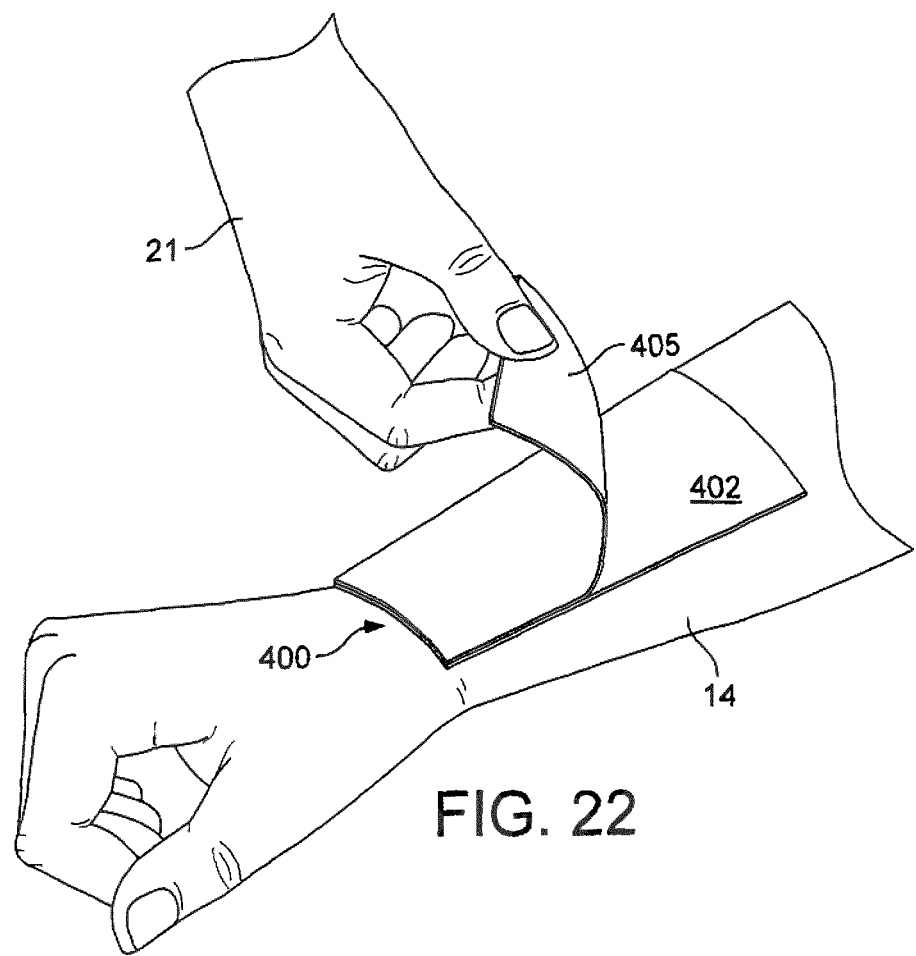
FIG. 22 is a perspective view showing the act of removal of the siliconised release layer of the skin closure device in accordance with the fourth embodiment of the invention, leaving just the cured adhesive layer in place on the patient's forearm.

FIG. 22 is a perspective view showing the physician's or nurse's hand 21 removing the siliconised release liner 405 from the adhesive layer 402 of the skin closure film after the curable molecules in the adhesive composition of the adhesive layer 402 have been cured. After removal of the siliconised release liner 405, only the cured adhesive composition layer 402 remains on the patient's forearm 14.

As mentioned above, in the cured state, the adhesive composition of the adhesive layer 402 is transformed from its initial viscoelastic state to an elastic state. In the elastic state, the adhesive composition layer 402 remains firmly stuck to the patient's skin but, by virtue of its elasticity, the adhesive layer is able to move with the patient's skin as the patient moves. The cured adhesive composition layer is an effective barrier to bacteria. Any bacteria that remained on the surface of the patient's skin after preliminary antibacterial swabbing become immobilised in the cured adhesive composition layer and migration to the site of the wound is thereby inhibited. The cured adhesive composition layer 402 is also a mechanical barrier against dirt and other foreign particles and substances.

The cured adhesive composition layer 402 of the skin closure film remains in position on the patient's skin over the wound 15. The skin closure film is breathable and allows moisture, including sweat, to escape from the pores of the patient's skin. Moreover, the cured adhesive composition layer 402 has good water resistance and does not require special care by the patient when bathing or showering. Preferably, the cured adhesive composition layer 402 is transparent to allow inspection of the underlying skin surface without needing to remove the skin closure film.

The adhesive composition layer 402 is gradually sloughed away with the shedding of skin cells from the surface of the patient's skin as wound healing progresses.

Although the first, second, third and fourth embodiments have been described above in terms of a particular construction for the laminated product, the present invention is not limited to such a construction.

For example, at least the first carrier layer or the first release liner may have a tab that is not coated with the adhesive composition, the tab serving to facilitate handling of the laminated product so that the carrier layer or the release liner can be separated from the adhesive composition layer without the adhesive composition layer coming into contact with the patient's fingers (for example, when a patient is applying a dressing to himself) or the physician's or nurse's fingers or gloves (for example, when a dressing, a surgical incision drape, a bacterial barrier or a wound closure device is being applied by a medical practitioner).

A non-adhesive-coated tab may also be provided on the second carrier layer of the wound dressing described in the first embodiment to assist in removal of the second carrier layer with the film of switched adhesive after the curable molecules in the adhesive composition layer have undergone their curing reaction to transform the adhesive composition layer from its tacky state to its non-tacky or low-tack state.

Similarly, a non-adhesive-coated tab may also be provided on the second release liner of the surgical incision drape, the bacterial barrier or the wound closure device described in the second to fourth embodiments to assist in removal of the second release liner from the adhesive composition layer after the curable molecules in the adhesive composition layer have undergone their curing reaction to transform the adhesive composition layer from its viscoelastic state to its elastic state.

The first release liner does not need to be formed of a light occlusive material. If the packaging for the laminated product is light occlusive, the first release liner may be transparent. However, in these circumstances, the first release liner will need to be removed quickly and the laminated product will need to be applied quickly to the patient's skin if the photoinitiator in the adhesive composition layer is activated by visible light. The need for quick deployment of the laminated product is not as critical for adhesive composition layers that use a photoinitiator responsive to UV light but not responsive to visible light.

Similarly, the second release liner does not need to have a light occlusive layer. However, if the second release liner in the second, third and fourth embodiments described above consists of two layers (a light occlusive layer as well as siliconised release liners 205, 305 and 405), the layers may be stuck together using a low peel strength adhesive. As an alternative, they may be heat laminated together.

The release liners may be siliconised paper rather than siliconised plastic films.

100% transparency is not essential for the second carrier layer or the second release liner. It may be semi-transparent provided that it allows sufficient light (UV light and/or visible light) to pass through it to enable photoinitiated radical reaction of the curable molecules in the underlying adhesive composition layer.

EXAMPLES

The invention will now be further illustrated with reference to Examples. Firstly, we will describe how exemplary oligomeric curable molecules for use in the switchable adhesive compositions of the present invention may be prepared.

Example of Synthesized Acrylate Oligomer

In Example 1 below, the constituents are listed in the order:
A Isocyanate
B Solvent, if present
C Catalyst
D Stabilizer for preventing premature switch during storage
E Hydroxyl containing methacrylate ester.

Example 1

|    | Component      | Amount (g) |
|----|----------------|------------|
| A  | Desmodur N3900 | 353.5      |
| B  | Ethyl acetate  | 234        |
| C  | DBTDL          | 0.314      |
| D  | Irganox 1010   | 2.02       |
| E1 | Bisomer PPM5 LI | 339.5     |
| E2 | Bisomer HPMA   | 144.1      |

Reaction 1. Synthesis of Methacrylated Oligomers

The reaction was carried out at 60° C. under stirring. The isocyanate-containing component, catalyst (if not added previously), solvent and inhibitor were placed in a reaction vessel and stirred. Then the hydroxyl-containing methacrylic ester was added slowly to avoid a steep rise in temperature and in order to maintain the reaction temperature below 70° C. Since two different hydroxyl-containing methacrylic esters were used, the one with the higher molecular weight was added first. The lower molecular weight hydroxyl-containing methacrylic ester was added later, after confirming by GPC measurements that the higher molecular weight hydroxyl-containing methacrylic ester had completely reacted. After all reactants been added, the temperature was raised to 70° C. and the mixture was left under stirring for a period of two hours.

Since the formation of the polyurethane adhesive also is based on the reaction between an isocyanate and a hydroxyl component, it is necessary that the oligomer is synthesized in a manner so that residual amounts of isocyanate or hydroxyl groups are kept to a minimum. In the synthesis described here, a slight excess of the lower molecular weight hydroxypropyl methacrylate was used, which was removed in a rotary evaporator at a temperature of 80° C. under an air inlet so that a pressure of around 2 mbar could be with maintained during the evaporation process. The removal of hydroxypropyl methacrylate was continued until the area representing hydroxypropyl methacrylate in the GPC chromatogram decreased to about 0.1%.

Examples of Switchable Adhesive Compositions Incorporating the Oligomeric Curable Molecules of Example 1

Examples 2 to 6 are examples of switchable adhesive compositions in accordance with the present invention formulated to include "mixed-in" curable oligomers from Example 1 above.

In Examples 2 to 6 below, the constituents are listed in the order:
F Baymedix AR602
G curable molecules/oligomer
H photoinitiator
I Catalyst
J Baymedix AP501

Example 2

| | Component | Amount (g) |
|---|---|---|
| F | Baymedix AR602 | 20.0 |
| G | Oligomer from Example 1 | 19.2 |
| H | Irgacure 369 | 0.39 |
| I | Tin(II) 2-ethylhexanoate | 0.091 |
| J | Baymedix AP501 | 1.92 |

Example 3

| | Component | Amount (g) |
|---|---|---|
| F | Baymedix AR602 | 20.0 |
| G | Oligomer from Example 1 | 19.2 |
| H | Irgacure 369 | 0.39 |
| I | Tin(II) 2-ethylhexanoate | 0.11 |
| J | Baymedix AP501 | 2.02 |

Example 4

| | Component | Amount (g) |
|---|---|---|
| F | Baymedix AR602 | 20.0 |
| G | Oligomer from Example 1 | 19.0 |
| H | Irgacure 369 | 0.37 |
| I | Tin(II) 2-ethylhexanoate | 0.064 |
| J | Baymedix AP501 | 2.13 |

Example 5

| | Component | Amount (g) |
|---|---|---|
| F | Baymedix AR602 | 20.0 |
| G | Oligomer from Example 1 | 19.2 |
| H | Irgacure 369 | 0.39 |
| I | Tin(II) 2-ethylhexanoate | 0.11 |
| J | Baymedix AP501 | 2.22 |

Example 6

| | Component | Amount (g) |
|---|---|---|
| F | Baymedix AR602 | 20.0 |
| G | Oligomer from Example 1 | 19.2 |
| H | Irgacure 369 | 0.39 |
| I | Tin(II) 2-ethylhexanoate | 0.11 |
| J | Baymedix AP501 | 2.33 |

Reaction 2. Preparation of Switchable Adhesive Compositions

All components in Examples 2 to 6 except for Baymedix AP501 were loaded into a sealable glass jar and mixed to a homogenous solution using a magnetic stirrer over a period of approximately 60 minutes under protection from ultraviolet sources.

In preparation for coating, the solution was vacuum boiled in order to remove all present air bubbles, whereafter Baymedix AP501 was gently blended into the solution avoiding any new dispersal of air. After stirring the solution for approximately 30 minute or until it had reached a viscosity similar to syrup, the resulting adhesive solution was then spread onto a release liner using a spreader having a gauge of 150 μm and left to dry at room temperature for 10 minutes.

The adhesive coating was then further dried in a ventilated fan assisted oven at 110° C. for an additional 10 minutes. After drying, the thickness of the adhesive coating was about 60-80 μm.

Peel Force Measurements

For one set of peeling studies, a 23 μm Hostaphan RNK 2600 (polyester) film was transferred to the exposed side of the adhesive in preparation for peel force measurements.

For a second set of peeling studies, a medical film was transferred to the exposed side of the adhesive. The carrier film attached to the flexible medical film was removed after attaching the adhesive laminate to skin.

Peel strengths were determined after a dwell time of 20 minutes using an Instron 5943 testing rig, equipped with a 100N load cell, according to FINAT test method FTM1, with the exception that high density polyethylene (HDPE) panels were used as the substrate surface and that a peeling rate of 100 mm/min crosshead speed 200 mm/s was used in order to collect all of the necessary data within the time frame of one peel force measurement.

Unswitched peel force was measured before exposing the adhesive to light while adhesive switching was achieved by exposing the adhesive film (adhered to the HDPE plate) to light through the PET carrier film backing with a light intensity of approximately 5 mW/cm$^2$ from a XeLED-Ni3UV-R4-365-E27-SS lamp having a narrow spectrum around 365 nm. Switching times for the different coatings were measured as the time between the starting time of irradiation and the time when the substantially instantaneous loss of tack occurred, during a continuous peel strength test of about 1.5 minutes (i.e., the adhesive was peeled for a period of time whilst being irradiated). This while the switched peel force was measured after that the peel force had reached a plateau value, which usually occurred 5-10 seconds after the switch time. Peel strengths and switch times were measured in quadruple and the average values of switch time and peel strength (before and after switch) were calculated.

Peel Force Measurements on Skin

One forearm of a group of volunteers was washed gently with water and ordinary soap and dried a few minutes before application of four test strips onto the volar aspect of each volunteer's cleaned forearm. The test strips consisted of the adhesive to be tested sandwiched in between a release liner (Transparent PET Release film, 50 um, silicone 1720, quality 1876) and a medical film (Code 48938), and measured 20×100 mm. The strips were applied in a room protected from any UV light. All strips were attached by rolling a standard Finat test roller three times forward and back over each tape at a speed of 1 cm per second, thus firming them to the skin in a controlled manner.

Figure 23:
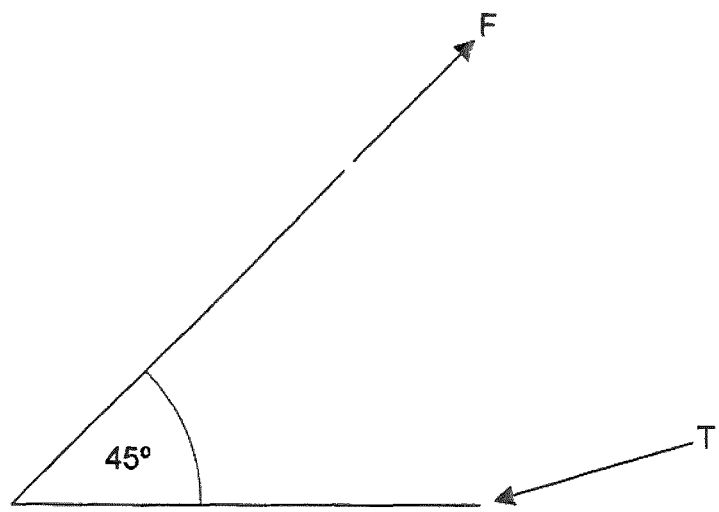
FIG. 23 is a schematic diagram showing peel force direction relative to the plane of application of an adhesive test strip during peel force tests on skin.

After one hour, two strips where peeled at a 135 degree angle using an Instron 5943 tensile tester machine with a speed of 600 mm/minute according to the illustration in FIG. 23.

The remaining two strips were then illuminated for about 10 seconds to effect switching using a XeLED-Ni3UV-R4-365-E27-SS light source held at a distance of approximately 20 cm from the strips. The peel forces were recorded and the average values were calculated.

Test Results

TABLE 2

Adhesive composition peel force and switch properties

| | Tests performed on HDPE | | | Tests performed on skin | |
|---|---|---|---|---|---|
| Example no | Peel force before switch (N/25 mm) | Peel force after switch (N/25 mm) | Switch time (s) | Peel force before switch (N/20 mm) | Peel force after switch (N/20 mm) |
| 2 | 3.09 | 0.038 | 1.9 | 2.69 | 0.16 |
| 3 | 1.78 | 0.036 | 1.8 | 1.96 | 0.15 |
| 4 | 1.54 | 0.034 | 2 | 1.55 | 0.1 |
| 5 | 1.58 | 0.038 | 2 | 0.96 | 0.09 |
| 6 | 1.02 | 0.033 | 2.1 | 0.65 | 0.07 |

From Table 2 above it can be seen that the initial peel force can be varied in a controlled fashion by adjusting the amount of the curing component Baymedix AP 501 from a low to a high value. Even though the data is not presented here, the addition of higher or lower amounts of the curing component Baymedix AP 501 than used in Examples 2 to 6 results in initial peel forces outside the ranges listed in the table.

Example of Synthesized Isocyanate Methacrylate Oligomer

In the Example below, the constituents are listed in the order:
K Isocyanate
L Solvent, if present
M Catalyst
N Stabilizer for preventing premature switch during storage
O Hydroxyl containing methacrylate ester.

Example 7

| | Component | Amount (g) |
|---|---|---|
| K | Desmodur N3600 | 20.3 |
| L | Ethyl acetate | 6.01 |
| M | Bismuth (III) neodecanoate | 0.086 |
| N | Irganox 1010 | 0.078 |
| O | Bisomer HPMA | 9.06 |

Reaction 3. Preparation of Isocyanate Functional Methacrylated Oligomers

The reaction was carried out at room temperature under stirring. All the components except for the hydroxyl functional methacrylate were added into a reagent bottle and mixed into a homogeneous solution, after which the hydroxyl functional methacrylate was added. The mixture was left overnight for the reaction to be completed. After confirming by GPC measurements that no residual hydroxyl functional acrylate was present, the isocyanate functional acrylate oligomer was ready to be used.

Gel Permeation Chromatography (GPC)

Samples were diluted with tetrahydrofuran in a ratio of 1:100 and injected in an amount of 20 μl into the injection valve of a Waters HPLC 1515 pump using a flow rate of 1 ml/min of tetrahydrofuran. The instrument was equipped with Styragel HR3 and HR1 columns connected to a Waters 2414 refractive index detector. Calibration was done with polystyrene standards.

Examples of Switchable Adhesive Compositions Incorporating the Oligomeric Curable Molecules of Example 7

Examples 8 to 10 are examples of switchable adhesive compositions in accordance with the present invention formulated to include "partially bound-in" oligomers from Example 7 above.

In Examples 8 to 10 below, the constituents are listed in the order:
F Baymedix AR602
P Curable molecules/oligomer from example 7
H Photoinitiator
L Ethyl acetate Example 8

| | Component | Amount (g) |
|---|---|---|
| F | Baymedix AR602 | 30.1 |
| P | Oligomer from Example 7 | 8.27 |
| H | Irgacure 369 | 0.37 |
| L | Ethyl acetate | 3.0 |

Example 9

| | Component | Amount (g) |
|---|---|---|
| F | Baymedix AR602 | 30.2 |
| P | Oligomer from Example 7 | 7.05 |
| H | Irgacure 369 | 0.359 |
| L | Ethyl acetate | 3.0 |

Example 10

| | Component | Amount (g) |
|---|---|---|
| F | Baymedix AR602 | 30.1 |
| P | Oligomer from Example 7 | 7.51 |
| H | Irgacure 369 | 0.359 |
| L | Ethyl acetate | 3.0 |

Test Results

In Table 3, test results are presented for Examples 8 to 10.

TABLE 3

Adhesive composition peel force and switch properties

| | Tests performed on HDPE | | | Tests performed on skin | |
|---|---|---|---|---|---|
| Example no. | Peel force before switch (N/25 mm) | Peel force after switch (N/25 mm) | Switch time (s) | Peel force before switch (N/20 mm) | Peel force after switch (N/20 mm) |
| 8 | 0.64 | 0.016 | 1.6 | 0.93 | 0.07 |
| 9 | 1.93 | 0.017 | 1.5 | 2.44 | 0.15 |
| 10 | 1.42 | 0.016 | 1.4 | 1.63 | 0.13 |

Examples of Switchable Adhesive Compositions Incorporating Curable Moieties Fully Bound-in to a Polyurethane Adhesive Component Following are examples of switchable adhesive compositions in accordance with the present invention formulated to include "fully bound-in" curable moieties that are bound to the polyurethane polyol backbone.

Reaction 4. Synthesis of Methacrylated Polyol

The reaction was carried out at room temperature under stirring and all the reactants except for diisocyanate were added at the same time into a reagent bottle and left over night for the reaction to be completed.

Reaction 5. Preparation of Switchable Adhesive Compositions

After confirming by GPC measurements that no residual acrylated isocyanate was present, the solution was vacuum boiled in order to remove all present air bubbles, whereafter diisocyanate was gently blended into the solution avoiding any new dispersal of air. After stirring the solution for approximately 10 minute or until it had reached a viscosity similar to syrup, the resulting adhesive solution was then spread onto a release liner using a spreader having a gauge of 150 μm and left to dry at room temperature for 10 minutes.

The adhesive coating was then further dried in a ventilated fan assisted oven at 110° C. for an additional 10 minutes. After drying, the thickness of the adhesive coating was about 60-80 μm.

Examples of Switchable Adhesives Incorporating Polyol with "Fully Bound-in" Methacrylate Moieties.

In Examples 11 to 13 below, the constituents are listed in the order:
F Polyol
L Solvent
M Catalyst
Q Acrylated isocyanate
H Photoinitiator
J Diisocyanate

Example 11

| | Component | Amount (g) |
|---|---|---|
| F | Baymedix AR602 | 30.1 |
| L | Ethyl acetate | 6.0 |
| M | Bismuth (III) neodecanoate | 0.043 |
| Q | 2-Isocyanatoethyl methacrylate | 1.30 |
| H | Irgacure 369 | 0.372 |
| J | Baymedix AP501 | 2.95 |

Example 12

| | Component | Amount (g) |
|---|---|---|
| F | Baymedix AR602 | 30.2 |
| L | Ethyl acetate | 6.0 |
| M | Bismuth (III) neodecanoate | 0.038 |
| Q | 2-Isocyanatoethyl methacrylate | 1.14 |
| H | Irgacure 369 | 0.351 |
| J | Baymedix AP501 | 3.20 |

Example 13

| | Component | Amount (g) |
|---|---|---|
| F | Baymedix AR602 | 30.1 |
| L | Ethyl acetate | 6.0 |
| M | Bismuth (III) neodecanoate | 0.058 |
| Q | 2-Isocyanatoethyl methacrylate | 1.02 |
| H | Irgacure 369 | 0.345 |
| J | Baymedix AP501 | 2.88 |

Test Results

In table 4, the test results are presented for Examples 11 to 13.

TABLE 4

Adhesive composition peel force and switch properties

| | Tests performed on HDPE | | | Tests performed on skin | |
|---|---|---|---|---|---|
| Example no. | Peel force before switch (N/25 mm) | Peel force after switch (N/25 mm) | Switch time (s) | Peel force before switch (N/20 mm) | Peel force after switch (N/20 mm) |
| 11 | 1.80 | 0.014 | 1.4 | 1.83 | 0.12 |
| 12 | 0.24 | 0.013 | 1.4 | 0.64 | 0.078 |
| 13 | 2.29 | 0.010 | 1.4 | 2.37 | 0.11 |

Non-Medical Applications

The present invention is not limited to use in adhesive medical products. Examples of other technical applications are listed below in Table 5.

TABLE 5

Non-medical applications

| Application | Format | Description |
|---|---|---|
| Labels, posters or Notices | A two or three-layer product. | Labels comprising an adhesive according to the invention can be used in product tags, pricing tags, advertisement posters put onto the varnish of vehicles. There will result a strong fixation and an easy removal without any adhesive residues left on the surface Or, in the case of a two layer film, easily removable residues after switching the adhesive. |
| Protection Films | A two or three-layer product. | Goods may get scratched during transportation, storage, handling etc; by using an adhesive according to the invention in combination with protective films, the goods will be protected from scratches and similar surface damage. When removing the film, no strong peeling force is necessary and, in the case of a three layer film, no adhesive residues left on the goods: or, in the case of a two layer film, easily removable residues after switching the adhesive. |
| Fixation of Sensitive Parts During Manufacture or Transport | A three-layer product. | Products and/or product parts that are very fragile and/or have a sensitive surface can be adhered to a substrate using an adhesive according to the present invention during transportation or manufacturing processes for achieving a very accurate position and fixation; after processing, the product can still be detached from the adhesive when desired without high peel forces and without leaving residues on its surface. |
| Shop Floor or Wall Marker Labels | A two-layer product. | Using an adhesive according to the present invention on shop floor marker labels in different shapes, a very strong fixation to the floor or wall surface is possible. When the marker label is removed, adhesive residues may be left on the surface which are very easy to rub off when switched. |
| Wallpaper | A three-layer product. | Using an adhesive according to the invention on wall paper, a very strong fixation to the wall is possible. When the wallpaper is removed after switching the adhesive, the wall surface is left without any damage or residuals. |
| Masking or Fixation Tapes (fixation of non-fragile or non-delicate articles) | A two or three-layer product | Using an adhesive according to the invention for the purpose of temporary fixation or masking, a very strong fixation to the surface is possible. When the tape is removed after switching the adhesive using a three layer design, the surface is left without any residues or, in the case of a two layer film, easily removable residues after switching the adhesive. |
| De-bond on demand (DOD) applications, such as opening of packages and recycling of different materials in a product by detaching them after the end of service lifetime. | A two or three-layer product. | Using an adhesive according to the invention for the purpose of strongly attaching different components into a product or package. When the product or package needs to be disassembled, the light occlusive layer is removed and, after switching the adhesive, the different parts can easily be detached. Should adhesive residues be left on the component or product surface, these can be easily removed after switching the adhesive. |

TABLE 6

Table of Suppliers

| Component | Description | Company |
|---|---|---|
| Desmodur N 3900 | Hexamethylene polyisocyanate (iminooxadiazindione) NCO content 23.7 w/w % | Covestro UK Ltd. |
| Desmodur N 3600 | Hexamethylene polyisocyanate (isocyanurate) NCO content 23.0 w/w% | Covestro UK Ltd. |
| Bisomer HPMA | Hydroxypropyl methacrylate | GEO Specialty Chemicals UK Ltd |
| Bisomer PPM5 LI | Polypropyleneglycol monomethacrylate Hydroxyl value 149.6 mgKOH/g | GEO Specialty Chemicals UK Ltd |
| Irganox 1010 | Pentaerythritol Tetrakis(3-(3,5-di-tert-butyl-4-hydroxyphenyl) propionate | BASF AG |
| Irgacure 369 | 2-Benzyl-2-dimethylamino-1-(4-morpholinophenyl)-butanone-1 | BASF AG |
| Code 48938 | Medical film | Shanghai ISO Medical Products Co. Ltd |
| HDPE panels | Panels for peel test measurements | ChemInstrument Inc. |
| Hostaphan RNK 2600 | Polyester film | Mitsubishi Polyester Film GmbH |
| Transparent PET Release film, 50 um, silicone 1720, quality 1876 | Release liner | Huhtamaki Oyj |
| Baymedix AR 602 | Polyether polyol based on a tetra-functional starter molecule. Hydroxyl value 34 mgKOH/g | Covestro UK Ltd. |
| Baymedix AP501 | Aliphatic NCO-terminated prepolymer based on hexamethylene diisocyanate. NCO content 12.9 w/w % | Covestro UK Ltd. |
| Catalyst | Dibutyl tin dilaurate | Sigma Aldrich |
| Catalyst | Tin(II) 2-ethylhexanoate | Sigma Aldrich |
| Catalyst | Bismuth (III) neodecanoate | Sigma Aldrich |
| XeLED-Ni3UV-R4-365-E27-SS | LED ultra violet light source | Xenopus Electronix |
| Isocyanate methacrylate | 2-Isocyanatoethyl methacrylate | Sigma Aldrich |

What is claimed is:

1. A switchable adhesive composition comprising, in proportions by weight based on the weight of the composition:
    10% to 99.89% of an adhesive component;
    5% to 80% of at least one curable molecule that is curable by free radical polymerisation;
    and
    0.05% to 10% of photoinitiator,
wherein the adhesive component is a polymer comprised of:
    (i) a polyether or polyester polyol that is capable of undergoing cross-linking with isocyanate by a mechanism other than free radical polymerisation, said polyether or polyester polyol having an average of more than one functional group containing an active hydrogen atom and having a weight average molecular weight in the range 2,000 to 20,000 dalton; and
    (ii) at least one isocyanate having an average of more than one isocyanate functions to cross-link said material and having a weight average molecular weight in the range 100 to 1,000,000 dalton;
    characterized in that the polyether or polyester polyol has three or more hydroxyl functions, further characterized in that the at least one curable molecule comprises at least 2 unsaturated functional groups, and further characterized in that the switchable adhesive composition is adapted to irreversibly switch from a tacky state to a low-tack state responsive to irradiation by visible light or UV light.

2. A switchable adhesive composition as claimed in claim 1, wherein the curable molecules are oligomers of at least one of the following formulae (I) to (V):

$$CA(BA)_nC \quad (I)$$

where n is 0, 1, 2, 3 or 4,
A is a diisocyanate, a diepoxide, a diol or a dicarboxylic acid;
B is a diol when A is a diisocyanate or a dicarboxylic acid; B is a dicarboxylic acid when A is a diepoxide or a diol;
C is a hydroxyl containing acrylate ester when A is a diisocyanate or a dicarboxylic acid;
C is an acrylic acid when A is a diepoxide or a diol;

$$C_2E(BCE)_nC_2 \quad (II)$$

where n is 0, 1, 2, 3 or 4,
E is a tri-isocyanate, a triepoxide, a triol or a tricarboxylic acid;
B is a diol when E is a tri-isocyanate or a tricarboxylic acid; B is a dicarboxylic acid when E is a triepoxide or a triol;
C is a hydroxyl containing acrylate ester when E is a tri-isocyanate or a tricarboxylic acid; C is an acrylic acid when E is a triepoxide or a triol;

$$E_{(2n+1)}F_nC_{(3n+3)} \quad (III)$$

where n is 0, 1, 2, 3 or 4,
E is a tri-isocyanate, a triepoxide, a triol or a tricarboxylic acid;
F is a triol when E is a tri-isocyanate or a tricarboxylic acid; F is a tricarboxylic acid when E is a triepoxide or a triol;
C is a hydroxyl containing acrylate ester when E is a tri-isocyanate or a tricarboxylic acid; C is an acrylic acid when E is a triepoxide or a triol;

$$G_{(n+1)}B_nC_{(2n+4)} \quad (IV)$$

where n is 0, 1, 2, 3 or 4,
G is a tetra-isocyanate, a tetra-epoxide, a tetra-ol or a tetra-carboxylic acid;
B is a diol when G is a tetra-isocyanate or a tetra-carboxylic acid; B is a dicarboxylic acid when G is a tetra-epoxide or a tetra-ol;
C is a hydroxyl containing acrylate ester when G is a tetra-isocyanate or a tetra-carboxylic acid; C is a dicarboxylic acid when G is a tetra-epoxide or a tetra-ol;

$$DC_3 \quad (V)$$

where D is a symmetrical isocyanurate trimeric ring structure or an asymmetric trimeric iminooxadiazinedione ring structure consisting of three diisocyanate molecules, or a linear trimeric biuret or allophanate structure,
C is a hydroxyl containing acrylate ester;
and wherein the oligomers have a weight average molecular weight of at least 500 dalton.

3. A switchable adhesive composition as claimed in claim 2, wherein the oligomers have a weight average molecular weight in the range 500 to 10,000 dalton.

4. A switchable adhesive composition as claimed in claim 1, wherein the curable molecules are unsaturated compounds.

5. A switchable adhesive composition as claimed in claim 4, wherein the curable molecules are selected from methacrylic acid esters, acrylic acid esters of alcohols, methacrylic acid esters of alcohols, glycols, pentaerythritol, trimethylpropane, glycerol, aliphatic epoxides, aromatic epoxides including bisphenol A epoxides, aliphatic urethanes, aromatic urethanes, silicones, polyesters, polyethers, or mixtures thereof.

6. A switchable adhesive composition as claimed in claim 1, comprising, in proportions by weight based on the weight of the composition:
    40% to 98% of adhesive component;
    2% to 60% of curable molecules curable by free radical polymerization; and
    0.5% to 5% of photoinitiator.

7. A switchable adhesive composition as claimed in claim 1, comprising, in proportions by weight based on the weight of the composition:
    60% to 95% of adhesive component;
    5% to 40% of curable molecules curable by free radical polymerisation; and
    0.5% to 5% of photoinitiator.

8. A switchable adhesive composition as claimed in claim 1, comprising, in proportions by weight based on the weight of the composition:
    70% to 85% of adhesive component;
    15% to 30% of curable molecules curable by free radical polymerisation; and
    0.5% to 2% of photoinitiator.

9. A switchable adhesive composition comprising, in proportions by weight based on the weight of the composition:
    90% to 99.95% of an adhesive component; and
    0.05% to 10% of photoinitiator;
wherein the adhesive component is a polymer comprising:
    (i) a polyether or polyester polyol that is capable of undergoing cross-linking with isocyanate by a mechanism other than free radical polymerisation, said polyether or polyester polyol having an average of more than one functional group containing an active hydrogen atom, a proportion of the functional groups containing an active hydrogen atom being reacted with and bonded to a curable moiety that is curable by free radical polymerisation, such that the adhesive composition comprises up to 98% by weight of such curable moieties, and having a weight average molecular weight in the range 2,000 to 20,000 dalton, and (ii) at least one isocyanate having an average of more than one isocyanate functions to cross-link said material and having a weight average molecular weight in the range 100 to 1,000,000 dalton;

characterized in that the polyether or polyester polyol has three or more hydroxyl functions, and further characterized in that the switchable adhesive composition is adapted to irreversibly switch from a tacky state to a low-tack state responsive to irradiation by visible light or UV light.

10. A switchable adhesive composition as claimed in claim 9, wherein at least 20% of the available functional groups comprising an active hydrogen atom in the material or materials capable of undergoing cross-linking with isocyanate other than by free radical polymerisation are bonded to curable moieties.

11. A switchable adhesive composition as claimed in claim 9, comprising at least 0.1% wt., based on the weight of the adhesive composition, of at least one curable acrylate moiety bound to the isocyanate.

12. A switchable adhesive composition as claimed in claim 9, wherein said curable moiety comprises an isocyanate group with a pendant acrylate function or pendant acrylate functions bonded to said material capable of undergoing cross-linking with isocyanate.

13. A switchable adhesive composition as claimed in claim 12, wherein said curable moiety comprises an isocyanato $C_{1-6}$alkyl 2-$C_{0-6}$alkylacrylate or an isocyanato $C_{1-3}$alkyl 2-$C_{0-3}$alkylacrylates.

14. A switchable adhesive composition as claimed in claim 13, wherein said curable moieties are selected from isocyanatoethyl acrylate, isocyanatoethyl methacrylate isocyanatoethyl 2-ethylacrylate, acrylic acid, or methacrylic acid.

15. A switchable adhesive composition as claimed in claim 9, wherein the polyol is a polyether polyol.

16. A switchable adhesive composition as claimed in claim 9, wherein the polyol is a polyester polyol.

17. A switchable adhesive composition as claimed in claim 9, wherein the polyol has an average of more than three and fewer than six hydroxyl functions.

18. A switchable adhesive composition as claimed in claim 9, wherein the weight average molecular weight of the isocyanate is in the range 100 to 2000 dalton.

19. A switchable adhesive composition as claimed in claim 9, wherein the isocyanate is selected from hexamethylene diisocyanate, isophorone diisocyanate, toluene 2,4-diisocyanate, 4,4'-methylenebis(phenyl isocyanate), 4,4'-methylenebis(cyclohexyl isocyanate), or their homopolymers.

20. A switchable adhesive composition as claimed in claim 1, wherein the isocyanate is a diisocyanate terminated reaction product with diol.

21. A switchable adhesive composition as claimed in claim 1, wherein the isocyanate is methacrylated oligomer having an average isocyanate functionality of at least two.

22. A switchable adhesive composition as claimed in claim 1, wherein the photoinitiator is selected from titanocene photoinitiators; dye/co-initiator systems including thionine/triethanolamine; dye/borate salt systems; dye/peroxide systems; or 1,2-diketone/co-initiator systems, including camphor-quinone/tertiary amine.

23. A switchable adhesive composition as claimed in claim 1, wherein the photoinitiator is reactive to visible light.

24. A switchable adhesive composition as claimed in claim 1, wherein the reduction in peel force of the adhesive after switching is 30 to 99% when determined according to FINAT test method FTM1 using high density polyethylene (HDPE) panels as the substrate surface with a peeling rate of 100 mm/min and a crosshead speed of 200 mm/s.

25. A switchable adhesive as composition claimed in claim 24, wherein the reduction in peel force of the adhesive after switching is 50 to 95%.

26. An adhesive medical product comprising a switchable adhesive composition as claimed in claim 1.

27. An adhesive medical product as claimed in claim 26, wherein the adhesive medical product is an adhesive dressing including an absorbent wound pad.

28. An adhesive medical product as claimed in claim 26, wherein the adhesive medical product is a surgical incision drape.

29. An adhesive medical product as claimed in claim 26, wherein the adhesive medical product is a bacterial barrier for covering a wound, the bacterial barrier having no absorbent wound pad.

30. An adhesive medical product as claimed in claim 26, wherein the adhesive medical product is a skin closure device for closing together the edges of a wound.

31. An adhesive medical product as claimed in claim 26, comprising a layer of said switchable adhesive composition disposed between a first carrier film and a second carrier film wherein at least one of the carrier films includes a light occlusive layer on the surface of the carrier film remote from the adhesive composition.

32. An adhesive medical product as claimed in claim 31, wherein the carrier films have a low surface energy relative to skin so that the adhesive composition adheres preferentially to skin.

33. A method of treating a wound comprising applying an adhesive dressing as claimed in claim 27 to the wound site.

34. A method of preparing a site for surgical incision using a surgical incision drape as claimed in claim 32, the method comprising:

(i) removing the first carrier film from the surgical incision drape to expose one surface of the adhesive composition layer;

(ii) placing the exposed surface of the adhesive composition layer on a patient's skin at the intended site for surgical incision;

(iii) subjecting the adhesive composition layer to visible light or UV irradiation through the second carrier film to effect cure of the curable molecules in the adhesive composition; and (iv) after curing of the curable molecules or curable moieties in the adhesive composition, removing the second carrier film to expose the other surface of the cured adhesive composition layer.

35. A method of preparing a site for surgical incision as claimed in claim 34, further comprising cleaning the patient's skin in the area to which the surgical incision drape is to be applied to remove bacteria from the patient's skin.

36. A method of covering a wound using a bacterial barrier as claimed in claim 32, the method comprising:
  (i) removing the first carrier film from the bacterial barrier to expose one surface of the adhesive composition layer;
  (ii) placing the exposed surface of the adhesive composition layer on a patient's skin over the wound;
  (iii) subjecting the adhesive composition layer to visible light or UV irradiation through the second carrier film to effect cure of the curable molecules in the adhesive composition; and
  (iv) after curing of the curable molecules or curable moieties in the adhesive composition,
  removing the second carrier film to expose the other surface of the cured adhesive composition layer.

37. A method of covering a wound as claimed in claim 36, further comprising cleaning the patient's skin in the area to which the bacterial barrier is to be applied to remove bacteria from the patient's skin.

38. A method of closing the edges of a wound using a skin closure device as claimed in claim 32, the method comprising:
  (i) removing the first carrier film from the skin closure device to expose one surface of the adhesive composition layer;
  (ii) placing one end of the exposed surface of the adhesive composition layer on a patient's skin in the vicinity of one end of the wound;
  (iii) bringing the edges of the wound together and progressively applying the adhesive composition layer along said wound from said one end to the other end of the wound;
  (iv) subjecting the adhesive composition layer to visible light or UV irradiation through the second carrier film to effect cure of the curable molecules in the adhesive composition; and
  (iv) after curing of the curable molecules or curable moieties in the adhesive composition,
  removing the second carrier film to expose the other surface of the cured adhesive composition layer.

39. A method of closing the edges of a wound as claimed in claim 38, further comprising cleaning the patient's skin in the area to which the skin closure device is to be applied to remove bacteria from the patient's skin.

40. A method as claimed in claim 34, wherein said step of subjecting the adhesive composition layer to visible light or UV irradiation to effect cure of the curable molecules or curable moieties in the adhesive composition comprises removing an occlusive layer from the second carrier film prior to irradiation.

41. A switchable adhesive composition as claimed in claim 4, wherein the curable molecules have more than one unsaturated site.

42. A switchable adhesive composition as claimed in claim 10, wherein the curable moieties have more than one unsaturated site.

43. A switchable adhesive composition as claimed in claim 1, wherein the polyol is selected from ethoxylated or propoxylated species of glycerol, trimethylolpropane, pentaerythritol, dextrose, sorbitol, or di- or tri-ethers thereof.

44. A switchable adhesive composition as claimed in claim 9, wherein the polyol is selected from ethoxylated or propoxylated species of butyldiol, glycerol, trimethylolpropane, pentaerythritol, dextrose, sorbitol, or di- or tri-ethers thereof.

45. The switchable adhesive composition of claim 43, wherein the polyol is randomly polymerized from a mixture of ethylene oxide and propylene oxide or polymerized separately in succession.

46. The switchable adhesive composition of claim 44, wherein the polyol is randomly polymerized from a mixture of ethylene oxide and propylene oxide or polymerized separately in succession.

\* \* \* \* \*